United States Patent
Zadeh

(10) Patent No.: US 7,494,812 B2
(45) Date of Patent: Feb. 24, 2009

(54) GENERATION OF HUMAN REGULATORY T CELLS BY BACTERIAL TOXINS FOR THE TREATMENT OF INFLAMMATORY DISORDERS

(75) Inventor: Homayoun H. Zadeh, Calabasas, CA (US)

(73) Assignee: University of Southern California, Los Angeles, CA (US)

(*) Notice: Subject to any disclaimer, the term of this patent is extended or adjusted under 35 U.S.C. 154(b) by 457 days.

(21) Appl. No.: 10/817,506

(22) Filed: Apr. 1, 2004

(65) Prior Publication Data

US 2005/0032217 A1 Feb. 10, 2005

Related U.S. Application Data

(60) Provisional application No. 60/459,778, filed on Apr. 1, 2003.

(51) Int. Cl.
*C12N 5/02* (2006.01)

(52) U.S. Cl. ..................... 435/377; 435/320.1

(58) Field of Classification Search .................. None
See application file for complete search history.

(56) References Cited

U.S. PATENT DOCUMENTS

| 5,847,257 | A | | 12/1998 | Seo et al. | |
|---|---|---|---|---|---|
| 5,958,416 | A | | 9/1999 | Birnbaum et al. | |
| 5,993,803 | A | * | 11/1999 | Cohen et al. | 424/93.71 |
| 6,451,316 | B1 | | 9/2002 | Srivastava | |
| 2006/0177461 | A1 | * | 8/2006 | Young et al. | 424/185.1 |

* cited by examiner

*Primary Examiner*—James Ketter
(74) *Attorney, Agent, or Firm*—Hogan & Hartson LLP

(57) ABSTRACT

An adoptive immunotherapy using ex vivo-generated regulatory T cells may be used for the suppression of undesireable immune response. T cells are to be obtained from the patient's blood, and upon exposure to a set of toxins from the pathogen *A. actinomycetemcomitans*, the population of regulatory T cells will be enriched ex vivo and adoptively transferred back to the patient. The novel aspect of the present invention is that it generates large numbers of type 1 regulatory T cells, which secrete Interleukin-10.

19 Claims, 9 Drawing Sheets

GENERATION OF HUMAN REGULATORY T CELLS BY BACTERIAL TOXINS FOR THE TREATMENT OF INFLAMMATORY DISORDERS

RELATED APPLICATIONS

This application claims priority to U.S. Provisional Application Ser. No. 60/459,778, filed Apr. 1, 2003, the content of which is incorporated herein by reference.

STATEMENT REGARDING FEDERALLY SPONSORED RESEARCH OR DEVELOPMENT

This invention was made with government support under Contract No. DE010861 awarded by the National Institutes of Health. The government has certain rights in the invention.

BACKGROUND OF THE INVENTION

1. Field of the Invention

The present invention includes methods for inducing differentiation, selective enrichment and/or promoting proliferation of regulatory T cells. More particularly, the present invention relates to an adoptive immunotherapy using a composition enriched for a T cell population whose marker is $CD4^+CD25^+$ and expresses Interleukin (IL)-10.

2. Description of the State of Art

The immune response is an exceedingly complex and valuable homeostatic mechanism that has the ability to recognize foreign pathogens while avoiding reacting with constituents of our body; that is, we are tolerant of "self". The initial response to a foreign pathogen is called "innate immunity" and is characterized by the rapid migration of natural killer cells, macrophages, neutrophils, and other leukocytes to the site of the foreign pathogen. These cells can either phagocytose, digest, lyse, or secrete cytokines that lyse the pathogen in a short period of time. The innate immune response is not antigen-specific and is generally regarded as a first line of defense against foreign pathogens until the "adaptive immune response" can be generated. Both T cells and B cells participate in the adaptive immune response. A variety of mechanisms are involved in generating the adaptive immune response. A discussion of all the possible mechanisms of generating the adaptive immune response is beyond the scope of this section; however, some mechanisms which have been well-characterized include B cell recognition of antigen and subsequent activation to secrete antigen-specific antibodies and T cell activation by binding to antigen presenting cells.

B cell recognition involves the binding of antigen, such as bacterial cell wall, bacterial toxin, or a glyco-protein found on a viral membrane to the surface immunoglobulin receptors on B cells. The receptor binding transmits a signal to the interior of the B cell. This is what is commonly referred to in the art as "first signal." In some cases, only one signal is needed to activate the B cells. These antigens that can activate B cells without having to rely on T cell help are commonly referred to as T-independent antigens (or thymus-independent antigens). In other cases, a "second signal" is required and this is usually provided by T helper cells binding to the B cell. When T cell help is required for the activation of the B cell to a particular antigen, the antigen is then referred to as T-dependent antigen (or thymus-dependent antigen). In addition to binding to the surface receptors on the B cells, the antigen can also be internalized by the B cell and then digested into smaller fragment within the B cell and presented on the surface of B cells in the context of antigenic peptide-MHC class II molecules. These peptide-MHC class II molecules are recognized by T helper cells that bind to the B cell to provide the "second signal" needed for some antigens. Once the B cell has been activated, the B cells begin to secrete antibodies to the antigen that will eventually lead to the inactivation of the antigen. Another way for B cells to be activated is by contact with follicular dendritic cells (FDCs) within germinal centers of lymph nodes and spleen. The follicular dendritic cells trap antigen-antibody (Ag-Ab) complexes that circulate through the lymph node and spleen and the FDCs present these to B cells to activate them.

Another well-characterized mechanism of adaptive immune response to antigens is the activation of T cells by binding to antigen presenting cells such as macrophages and dendritic cells. T cells compose a cell lineage, which plays a central role in the immune system as a system of biophylaxis against various pathogens. T cells are largely classified into $CD4^+$ T cells and $CD8^+$ T cells. In particular, the former T cells can be classified, depending on cytokine-producing patterns at certain differentiation and maturation stages after stimulation with antigens, into, for instance, Th1 cells producing mainly IFN-$\gamma$ and Th2 cells producing IL-4. Generally, the former and the latter T cells are deeply involved in biophylaxis as cellular immunity and as humoral immunity, respectively. The immune response is responsible for eliminating pathogens and acquiring resistance to infection based on a delicate balance resulting from functions of such T cells with varied characteristics. It is known that in the normal immune response, a mechanism works to eliminate foreign nonself antigens, but the mechanism does not eliminate autoantigens, which make an organism because of the established immunologic tolerance. However, overresponse of the immune system against autoantigens causes a so-called autoimmune disease. As described above, immunological tolerance against autoantigens is not an absolute mechanism. The mechanisms by which various immunological tolerances are induced are known in a T cell level. One of such mechanisms, called central tolerance, eliminates autoreactive T cell clones in the thymus (Kisielow, P., et al., *Nature*, 333:742-746 (1988)); and another mechanism, called peripheral tolerance, controls autoreactive T cells outside the thymus. Known to be included in the latter mechanism are induction of cell death or of anergy against self-antigens (Rocha, B., et al., *Science*, 251:1225-1228 (1991); Jenkins, M. K., et al., *J. Exp. Med.*, 165:302-319 (1987)), and active suppression by regulatory T cells (Shevach, E. M., *Annu. Rev. Immunol.*, 18:423-449 (2000)). The regulatory T cell is a new, recently proposed concept of T cells, and is defined as having a suppressive action against other T cells. The immune response is operated based on a delicate balance. For example, the above Th1 cells and Th2 cells function antagonistically to their respective immune response, and it has become known that one acts as regulatory T cells on the other. However, verification of the presence of a cell population as regulatory T cells and property analysis thereof has been a point of considerable debate throughout the recent history of immunology. Such regulatory T cells have been studied in vitro or in vivo as cells capable of suppressing or regulating certain immune responses, so that the T cells have been reported as different cell populations according to the cell surface markers, the types of cytokines produced, suppressive and regulatory mechanisms and the like (Roncarolo, M. G., et al., *Curr. Opinion. Immunol.*, 12:676-683 (2000)).

The most studied cell population among these regulatory T cells is a T cell population whose marker is $CD4^+CD25^+$ described below. This T cell population has been mainly studied in species of non-human organisms, such as mice and rats. The property analysis of the T cell population has been performed using as an index the fact that organ-specific autoimmune diseases (for example, thyroiditis, insulin-dependent diabetes mellitus, colitis) are induced by transferring T cells, from which certain T cells have been removed using expression of a particular cell surface molecule as an index, into T cell- and B cell-deficient SCID mice or rats (Sakaguchi, S., et al., *J. Exp. Med.*, 161:72 (1985); Itoh, M., et al., *J. Immunol.*, 162:5317-5326 (1999)). Specifically, $CD25^+$, $RT6.1^+$ (expressed in most mature T cells in rat), CD5 highly positive, or CD45RB weakly positive (mice) or CD45RC weakly positive (rats) cells are removed from the $CD4^+$ spleen cells of normal mice or rats, and then the remaining T cells are transferred to T cell- and B cell-deficient SCID mice or rats, thereby inducing organ-specific autoimmune diseases. To date, no such regulatory T cell-specific marker has been observed. That is, the above marker cannot be directly related to the function of regulatory T cells and it represents merely a state of cells being activated, that of cells being stimulated with antigens, or that of cells being immunological memory. However, the regulatory T cell population has been further analyzed using as an index the fact that the cell population is capable of suppressing autoimmune disease and autoimmune inflammation when a certain cell population is transferred, in addition to being capable of inducing organ-specific autoimmune disease in immunodeficient animals (Itoh, M., et al., *J. Immunol.*, 162:5317-5326 (1999); Sakaguchi, S., et al., *J. Immunol.*, 155:1151-1164 (1995); Asano, M., et al., *J. Exp. Med.*, 184:387-396 (1996); Read, S., et al., *J. Exp. Med.*, 192:295-302 (2000); Salomon, B., et al., *Immunity*, 12:431-440 (2000); Stephens, L. A., et al., *J. Immunol*, 165:3105-3110 (2000)). Therefore, it is now known that a $CD4^+CD25^+$ T cell population is capable of use as a marker of the regulatory T cells, conventionally.

Though $CD4^+CD25^+$ regulatory T cells have been identified in mice and rats as described above, several groups just recently reported in 2001 the presence of similar cells in humans (Jonuleit, H., et al., *J. Exp. Med.*, 193:1285-1294 (2001); Levings, M. K., et al., *J. Exp. Med.*, 193:1295-1301 (2001); Dieckmann, D., et al., *J. Exp. Med.*, 193:1303-1310 (2001); Taama, L. S., et al., *Eur. J. Immunol.*, 31:1122-1131 (2001); Stephens, L. A., et al., *Eur. J. Immunol.*, 31:1247-1245 (2001); Baecher-Allan, C., et al., *J. Immunol.*, 167: 1245-1253 (2001)). The basis of these reports is that a cell population isolated from human peripheral blood, when expression of CD4 and CD25 known for mice is used as an index, has properties equivalent to those reported for mice, in terms of various cell surface markers, anergy of cells to stimulation for activation, types of cytokines produced, in vitro proliferation inhibitory function of normal T cells, the mechanism thereof, and the like. Specifically, $CD4^+CD25^+$ T cells isolated from human peripheral blood express $CD45R0^+$ memory T cell markers, and compared to $CD4^+CD25^-$ T cells, highly express activation markers such as HLA-DR. Further, $CD4^+CD25^+$ T cells constantly express CTLA-4 within the cells, and the expression of CTLA-4 is enhanced by stimulation. Furthermore, some stimulations such as stimulation with anti-CD3 antibodies, stimulation with anti-CD3 antibodies and anti-CD28 antibodies, stimulation with allogeneic mature dendritic cells (allogeneic mature DC) do not cause $CD4^+CD25^+$ regulatory T cells to synthesize DNA and to produce cytokines. That is, $CD4^+CD25^+$ regulatory T cells are in an anergic state (anergy) following stimulation with antigens. Stimulation with cytokines, such as IL-2, IL-4, IL-15, in addition to that with anti-CD3 and anti-CD28 antibodies enhance the ability of $CD4^+CD25^+$ regulatory T cells to synthesize DNA, but the ability is not comparable to that of $CD4^+CD25^-$ T cells. When $CD4^+CD25^-$ T cells are stimulated with anti-CD3 antibodies or allogeneic mature DC in the presence of $CD4^+CD25^+$ regulatory T cells, in comparison with that in the absence of $CD4^+CD25^+$ regulatory T cells, proliferation inhibitory action is observed in a $CD4^+CD25^+$ regulatory T cell number-dependent manner. $CD4^+CD25^+$ regulatory T cells have ability to produce suppressor cytokines, such as IL-10 and TGF-β-1, which is lower than that of mice. However, it has been reported that the proliferation inhibitory action against $CD4^+CD25^-$ T cells is not canceled by neutralizing antibodies against these cytokines and the inhibitory action requires direct intercellular contact between $CD4^+CD25^-$ T cells and $CD4^+CD25^+$ regulatory T cells. Though the presence of $CD4^+CD25^+$ regulatory T cells in mice, rats and humans has been reported, and the property is being analyzed, detailed mechanisms of differentiation and suppressive action of these cells are still in the process of being elucidated, and no specific marker has been found so far.

Moreover, regulatory T cells, which are induced in a mouse and a human by repeated stimulation with allogeneic antigens or allogeneic immature DC in the presence of IL-10 have been also reported (Groux, H., et al., *Nature*, 389:737-742 (1997); Jonuliet, H., et al., *J. Exp. Med.*, 192:1213-1222 (2000)). Unlike Th1 and Th2 cells, these cells called Tr1 cells are characterized by producing high levels of IL-10, moderate levels of TGF-β-1, IFN-γ and IL-5, low levels of IL-2, and no IL-4. Similar to $CD4^+CD25^+$ regulatory T cells, Tr1 cells are anergic, and the T cell-suppressive mechanism can be partially explained by the IL-10 and TGF-β1 produced. However, whether Tr1 cells and $CD4^+CD25^+$ regulatory T cells are T cell subsets, which are totally different from each other, or are the same cells but which differ in their differentiation activation stage remains unknown.

Using expression of regulatory T cell markers CD4 and CD25, known among mice and rats, as an index, $CD4^+CD25^+$ T cells have been isolated from human peripheral blood. Thus, the isolated T cells have been confirmed to share similar functions with other known cell surface markers of mice or rats, suggesting the presence of $CD4^+CD25^+$ regulatory T cells in humans.

These T cells are of a rare cell population, which accounts for merely 5 to 10% of $CD4^+$ T cells of peripheral blood, and are anergic to stimulation for activation and proliferation. In this case, cell proliferation can be promoted by stimulating with cytokines, such as IL-2, IL-4 and IL-15, in addition to anti-CD3 antibodies and anti-CD28 antibodies. However, this is not at a sufficient level for clinical applications, such as an application that involves increasing cell count and transferring the cells into a human.

Since regulatory T cells act suppressively on autoimmune disease, transplant rejection, graft versus host disease (GVHD) when transferred into an animal (Hara, M., et al., *J. Immunol.*, 166:3789-3796 (2001); Taylor, P. A., et al., *J. Exp. Med.*, 193:1311-1317(2001)), it is considered that regulatory T cells may be applied to cellular medicine using their immunosuppressive action to treat autoimmune disease, transplantation or the like. Development of a pharmaceutical composition which promotes proliferation of regulatory T cells, or development of a therapy which involves treating ex-vivo peripheral blood or myeloma cells collected from patients or volunteers, allowing regulatory T cells to proliferate, and returning the cells into the bodies of patients, is being considered.

Pathogens

A recent report suggested that *Helicobacter hepaticus* infection may result in the induction of regulatory T cells that prevent bacteria-induced colitis (Kullberg, M. C., et al., *The Journal of Experimental Medicine*, 196:505 (2002)). It was hypothesized that the induction of these cells in response to gut flora may be a protective mechanism to limit tissue damage associated with inflammatory bowel disease. Conversely, during infection by *Leishmania major*, regulatory T cells accumulate in the skin, where they suppress the ability of effector T cells to eliminate the parasite from the site (Belkaid, Y., et al., *Nature*, 420:502 (2002)). The latter data suggested that the induction of regulatory T cells by a pathogen may constitute a virulence mechanism by which this organism suppresses and evades the host response.

*Actinobacillus actinomycetemcomitans* is a pathogenic bacterium with potent cytolytic potential. This pathogen has been implicated in a number of diseases, including periodontitis (Fives-Taylor, P. M., et al., *Periodontology*, 20:136 (2000)), as well as in a number of non-oral infections, e.g., cardiovascular, intracranial, thoracic and skin infections (van Winkelhoff, A. J., et al., *Periodontology*, 20:122 (2000)). Infections with *A. actinomycetemcomitans* are difficult to eradicate (Mombelli, A., R., et al., *Journal of Periodontology*, 65:827 (1994); Mombelli, A., et al., *Journal of Periodontology*, 65:820 (1994); Mombelli, A., et al., *Journal of Periodontology*, 71:14 (2000)). In chronic and aggressive forms of periodontitis, *A. actinomycetemcomitans* can persist as a chronic infection that may span years to decades (Slots, J., et al., *Journal Of Dental Research*, 63:412 (1984)). The underlying mechanisms responsible for the inability of the host to eliminate this infection and for the persistence of this organism have not been determined.

As discussed previously, failure of immunologic self-tolerance often leads to the development of autoimmune disease, which is estimated to afflict up to 5% of the population. Although the etiology of autoimmune disease is at present largely unknown, it is will documented that T cells are the key mediators of many autoimmune diseases, such as but not limited to inflammatory myopathy, Myasthenia Gravis, inflammatory polyneuropathies, Multiple Sclerosis, asthma, insulin-dependent diabetes mellitus (IDDM), autoimmune thyroiditis, autoimmune gastiritis accompanying pernicious anemia, and colitis.

There remains an urgent need to provide means to suppress the immune system using safe compositions that can be repeatedly administered, and which are effective to prevent and/or treat diseases amenable to treatment by supression of an immune response such as autoimmune diseases, transplant rejections, and cancer.

SUMMARY OF THE INVENTION

The purpose of the present invention is to provide a method for inducing differentiation and promoting proliferation of regulatory T cells.

In one aspect, the therapeutic composition of the present invention is obtained by inducing differentiation and promoting proliferation of regulatory T cells either in vivo or ex-vivo by the use of pathogenic toxins.

Inducing differentiation and promoting proliferation of regulatory T cells can be achieved ex vivo by incubating peripheral blood mononuclear cells (PBMC) in the presence of at least three proteins, cytolethal distending toxin (cdt), leukotoxin (ltx) and a heat shock protein, such as GroEL. These three proteins can be introduced naturally using the pathogenic organism *A. actinomycetemcomitans* or alternatively the expression sequences for these proteins may be cloned into an expression vector and either expressed directly in the PMBC or the proteins may be expressed in vitro, isolated and purified and then added directly to the PMBC.

In an alternate embodiment inducing differentiation and promoting proliferation of regulatory T cells can be achieved in vivo by administering directly to a patient in need of immune sytem modulation at least three proteins, cytolethal distending toxin (cdt), leukotoxin (ltx) and a heat shock protein, such as GroEL. These three proteins can be introduced in the form of a subunit vaccine or a whole organism vaccine wherein the pathogenic organism, is *A. actinomycetemcomitans*; alternatively, the expression sequences for these proteins may be cloned into an expression vector and expressed directly within the patient.

Yet another embodiment of the present invention relates to a method suppressing the immune system in a mammal. The method comprises: contacting PBMC with at least one toxin that induces differentiation and promotes proliferation of regulatory T cells having the marker $CD4^+$ $CD25^+$ T cells; isolating the regulatory T cells and administering to the mammal a composition enriched for $CD4^+$ $CD25^+$ T cells.

Yet another embodiment of the present invention relates to a method suppressing the immune system in a mammal. The method comprises: administering to a mammal an expression plasmid that expresses at least one toxin that induces differentiation and promotes proliferation of regulatory T cells having the marker $CD4^+$ $CD25^+$ T cells. The step of administering can be by any route, including, but not limited to, intravenous, intraperitoneal, subcutaneous, intradermal, intranodal, intramuscular, transdermal, inhaled, intranasal, rectal, vaginal, urethral, topical, oral, intraocular, intraarticular, intracranial, and intraspinal. In one embodiment, the step of administering is by a combination of intravenous and intranodal administration. In another aspect, the step of administering is by a combination of intraperitoneal and intranodal administration. In yet another aspect, the step of administering is by a combination of intradermal and intranodal administration.

Additional objects, advantages and novel features of this invention shall be set forth in part in the description that follows, and in part will become apparent to those skilled in the art upon examination of the following specification or may be learned by the practice of the invention. The objects and advantages of the invention may be realized and attained by means of the instrumentalities, combinations, compositions, and methods particularly pointed out in the appended claims.

BRIEF DESCRIPTION OF THE DRAWINGS

The accompanying drawings, which are incorporated in and form a part of the specification, illustrate the preferred embodiment of the present invention, and together with the description serve to explain the principles of the invention.

In the Drawings.

DETAILED DESCRIPTION OF INVENTION

Figure 1:
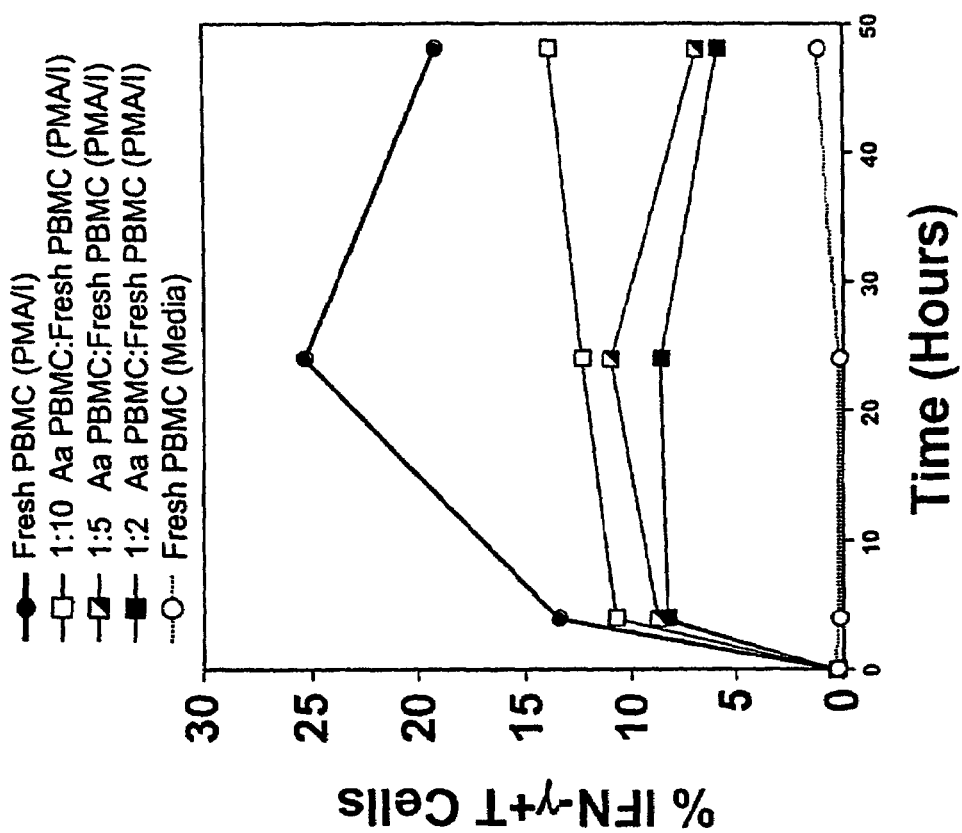
FIG. 1 shows induction of hypo-responsiveness in PBMC by co-culture with *A. actinomycetemcomitans* stimulated cells.

The present invention is founded on the suprising discovery that certain toxins produced by the pathogenic organism, *A. actinomycetemcomitans*, are capable of inducing differentiation and/or promoting proliferation of regulatory T cells. This basic discovery provides a platform for multiple novel immunization strategies as well as therapeutic compositions for modulating an immune response in a mammal. In particular, manipulation of regulatory T cells both in vivo and ex vivo will lead to new strategies for the treatment or prevention of autoimmune diseases, treatment of inflammatory disorders and prevention of transplant rejection.

Ex Vivo Manipulation

Inducing differentiation, selective enrichment and/or promoting proliferation of regulatory T cells can be achieved ex vivo by incubating whole blood or peripheral blood mononuclear cells (PBMC) in the presence of at least three proteins, cytolethal distending toxin (cdt), leukotoxin (ltx) and a heat shock protein, such as GroEL. These three proteins be introduced naturally to a quantity of whole blood using pathogenic organisms that express these toxins, crude extracts containing these proteins or alternatively the expression sequences for these proteins may be cloned into an expression vector and either expressed directly in the PMBC or the proteins may be expressed in vitro isolated and purified and then added directly to the PMBC.

Many Gram-negative bacterial pathogens synthesize cytolytic toxins as virulence factors. Most of these toxins generate pores in eukaryotic cell membranes. The ability to induce selective apoptosis of non-regulatory T cells, leading to selective enrichment of regulatory T cells may be a property of all cytolysins of Gram-negative bacteria.

Repeats in toxins (RTX) are members of a family of proteins that are synthesized by a diverse group of Gram-negative pathogens. Members of the RTX toxin family, including cytolytic toxins, metalloproteases and lipases, all share a common gene organization and distinctive structural features. RTX toxins are subdivided into two categories based on their target cell specificity. RTX hemolysins, such as *Escherichia coli* α-hemolysin (HlyA) and *Actinobacillus pleuropneumoniae* ApxI A are toxic to a wide range of cell types from many species, including erythrocytes, chicken embryo fibroblasts, rabbit granulocytes and mouse fibroblasts (3T3 cells). The other category of RTX proteins, which includes the leukotoxins of *Actinobacillus actinomycetemcomitans* (LtxA) and *Pasteurella haemolytica* (LktA), are toxic to restricted groups of cells in a species-specific fashion. For example, LtxA kills lymphocytes and granulocytes from humans, the Great Apes and Old World monkeys whereas LktA is specific for bovine lymphoid cells. Leukotoxin-producing bacteria that may be used according to the present invention, include but are not limited to *Actinobacillus actinomycetemcomitans*, *Mannheimia (Pasteurella) haemolytica*, and *Fusobacterium necrophorum*. CDT-producing bacteria that may be used according to the present invention, include but are not limited to *Actinobacillus actinomycetemcomitans*, *Escherichia coli Shigella dysentarie*, *Haemophilus ducreyi*, *Campylobacter upsaliensis*, *Campylobacter jejuni Helicobacter hepaticus*, and *Salmonella. enterica* serovar Typhi genome.

Incubation of *A. actinomycetemcomitans* in PBMC

In accordance with the present invention an adoptive immunotherapy using ex vivo-generated regulatory T cells may be used for the modulation of an undesireable immune response. Modulating an immune response comprises augmenting an immune response or down regulating or suppressing an immune response. Generation of the therapeutic composition of the present invention may be accomplished by essentially selecting for and enriching cells that have the CD4$^+$CD25$^+$ marker and secret Interleukin-10 (hereinafter referred to as regulatory T cells or Tr1 cells). Large quantities of Tr1 cells may be obtained by incubating a pathogenic organism capable of inducing differentiation and/or promoting proliferation of regulatory T cells with whole blood. The preferred pathogen according to the present invention is *A. actinomycetemcomitans*; however, it should be understood that other pathogens, such as those discussed above, having proteins that are homologous to cytolethal distending toxin (cdt), leukotoxin (ltx) and a heat shock protein, such as GroEL are also contemplated and within the purview of this invention. Genes that share greater than 80% homology and preferably 90% and most preferably 95% homology with cdt, ltx and GroEL would be useful in the present invention. Whole blood is preferably drawn from the patient to be treated, however large quantities of blood may be needed for some treatments and therefore blood may have to be collected from a number of sources having the proper blood type and pooled together. While whole blood may be utilized the overall efficiency of the process may be enhanced by isolating peripheral mononuclear blood cells (PMBC) and then incubating the pathogen with the PMBC. Isolation of PBMC is achieved by drawing venous blood from a mammal that has a disease amenable to treatment by supression of an immune response. Isolation of PBMC is well known to those skilled in the art, however one methodology that may be employed is Ficoll-Hypaque density gradient centrifugation (Böyum, A., et al., *Scandinavian Journal Of Clinical And Laboratory Investigation*, Supplement 97:77 (1968)) which is incorporated herein by reference. Once the whole blood or PMBC has been obtained the pathogenic organisms or extracts from the pathogenic organism is added and incubated. While bacterial cells may be used it is preferable to use their protein extracts.

Bacterial extracts may be prepared in numerous ways and will be understood by one skilled in the art. Briefly, *A. actinomycetemcomitans* was inoculated on solid media plates containing Trypticase Soy Broth (Becton Dickinson and Co., Cockeysville Md.) supplemented with Tripticase soy agar (1.5% w/v; Becton Dickinson and Co.), yeast extract (0.6% w/v; Difco Laboratories,) and 10% horse serum for 48 h at 37° C. in atmosphere supplemented with 5% $CO_2$. When necessary, the media were supplemented with spectinomycin (Spe, 50 μg/ml) or tetracycline (Tc, 6 μg/ml).

Bacteria and their extracellular products were harvested in previously described. *A. actinomycetemcomitans* cells were cultured as described above. Cultured cells and their extracellular products were removed from plates by washing the surfaces of plates with 3 ml of phosphate buffered saline (PBS), followed by centrifugation (7000 g for 30 min). The supernatant which contained the extracellular products of bacteria was used for the preparation of cell-free culture supernatant (CFCS). To prepare bacterial cellular extract (CE), cells were washed and frozen at −70° C. and thawed. Bacterial cells were then resuspended in a nonionic detergent (CelLytic B II; Sigma, St Louis, Mo.), Along with deoxyribonuclease (Dnase) I (5 μg/ml; Sigma) and incubated for 15 min with shaking at room temperature. Cellular debris and unlysed bacteria were removed by centrifugation (10,000 g for 30 min). The cell-free culture supernatant and cellular extract preparations were dialyzed overnight against PBS (SnakeSkin™ Dialysis Tubing; 10 kDa Molecular Weight cut-off, Pierce Chemical Co., Rockford, Ill.). The resultant fractions were sterilized by filtration through a 0.2 μm filter (Nalgene, Rochester, N.Y.). The protein concentration of bacterial preparations was measured by the Bradford method (Bio-Rad Laboratories, Richmond, Calif.) and samples were divided into aliquots and frozen at −70° C. until use. As a control for the cell-free culture supernatant preparation, the surface of un-inoculated agar plates was washed in the same manner with PBS. This demonstrated negligible presence of proteins. Hence, the preparation of bacterial extracellular material in this manner minimized the presence of bacterial media in the preparation, which is a problem when bacteria are grown in liquid media.

The concentration of bacterial extract to be used is determined for each batch, by performing an initial dose response experiment. The ED-50, which is the concentration of bacterial products, inducing half of the maximal level of apoptosis and $CD4^+CD25^+IL-10^+$ T cells will be selected. Incubation occurs for a period of time sufficient to pre-stimulate the cells. As discussed, cell-associated, as well as cell free culture supernatant of bacteria may used. The cell-associated bacterial extracts generally require about 48 hours of incubation, while the cell free culture supernatant of bacteria require about 72 hours. The time required to induce half of the maximal level of apoptosis and $CD4^+CD25^+IL-10^+$ T cells will be selected. The time period can be between 2 to 72 hours, and is preferably between 12 and 60 hours and more preferably between 24 and 48 hours depending on whether cells-associated or cell free cultures are used. All incubations are carried out at approximately 37° C., which is preferred by T cells. Additional proteins such as but not limited to cytokines, such as but not limited to Interleukin-10, Transforming growth factor (TGF)-β, Interleukin-2 may also be incubated with the PMBC. Additional molecules to enhance costimulation of T cells such as but not limited to antibody specific for CD28 may be added. Additional components of the pathogens such as but not limited to LPS may be added.

Following the incubation period the cultered cells are harvested, washed and the Tr1 cells are further isolated. To enrich for $CD4^+$ T cells, a negative selection scheme may be used, where cultured cells are labeled with a mixture of monoclonal antibodies specific for CD8, CD14, CD16 and CD19 (Becton Dickinson, San Jose, Calif.). The cells may then be washed and labeled with immunomagnetic beads conjugated with goat-anti-mouse IgG (Miltinyi Biotec, Auburn, Calif.). The immunomagnetically labeled cells are then passed through a column filled with steel wires and held near the magnet (MiniMACS; Miltinyi Biotec). Non-adherent cells are collected as source of enriched $CD4^+$ T cells. To isolate $CD4^+CD25^+$ T cells (Tr1 cells), a positive selection scheme may be used used, where enriched $CD4^+$ T cells were labeled with anti-CD25 monoclonal antibody (Becton Dickinson, San Jose, Calif.). The cells are then washed and labeled with immunomagnetic beads conjugated with goat-anti-mouse IgG (Miltinyi Biotec), followed by passage through the column held near the magnet (VarioMACS; Miltinyi Biotec, Auburn, Calif.). The non-adherent cells are washed off as $CD25^−$ cells and the magnet was removed to elute the adherent cells, which were $CD25^+$ cells. Immunofluorescent labeling was performed and demonstrated that the isolated cells were >90% $CD25^+$. Immunofluorescently-labeled cells are then processed on a FACSCalibur (Becton-Dickinson Immunocytometry Systems, San Jose, Calif.) flow cytometer equipped with an argon ion laser (488 nm), and the data analyzed using CellQuest software (Becton Dickinson). The data acquired by flow cytometry is limited to the cell subsets of interest by selection of electronic gates. Lymphocyte gates were selected on the basis of their forward and side scatter profiles. T cells were identified with anti-CD3 monoclonal antibody. The therapeutic composition of the present invention is thus enriched for Tr1 cells and can be administered to the mammal in need of treatment.

Accordingly, the method of the present invention preferably suppresses an immune response in a mammal such that the mammal is protected from a disease that is amenable to suppression of an immune response, including an autoimmune disease, transplant rejection and/or cancer and/or prevention of onset of the disease. As used herein, the phrase "protected from a disease" refers to reducing the symptoms of the disease; reducing the occurrence of the disease, and/or reducing the severity of the disease. Protecting a mammal can refer to the ability of a therapeutic composition of the present invention, when administered to a mammal, to prevent a disease from occurring and/or to cure or to alleviate disease symptoms, signs or causes. As such, to protect a mammal from a disease includes both preventing disease occurrence (prophylactic treatment) and treating a mammal that has a disease (therapeutic treatment). In particular, protecting a mammal from a disease is accomplished by suppressing an immune response in the mammal which may diminish an overactive or harmful immune response. The term, "disease" refers to any deviation from the normal health of a mammal and includes a state when disease symptoms are present, as well as conditions in which a deviation (e.g., infection, gene mutation, genetic defect, etc.) has occurred, but symptoms are not yet manifested.

More specifically, a therapeutic composition as described herein, when administered to a mammal by the method of the present invention, preferably produces a result which can include alleviation of the disease, elimination of the disease, reduction of inflammation associated with the disease, elimination of inflammation associated with the disease, prevention of a secondary disease resulting from the occurrence of a primary disease, prevention of the disease, and stimulation of effector cell immunity against the disease.

In one embodiment, the method and composition of the present invention are particularly useful for the prevention and treatment of autoimmune diseases, such as but not limited to allergies, inflammatory myopathy, Myasthenia Gravis, inflammatory polyneuropathies, Multiple Sclerosis, asthma, insulin-dependent diabetes mellitus (IDDM), autoimmune thyroiditis, autoimmune gastritis accompanying pernicious anemia, psoriasis, uveitis, rheumatoid arthritis, Systemic lupus erythematosus (SLE) and colitis. Additional application of this method may be in the prevention of transplant rejection, such as solid organ transplants (kidney, heart, lung, liver, pancreas), cell and tissue transplant rejection (bone marrow transplantation, stem cell transplantation, pancreatic islet transplantation, corneal transplantation, lens transplation), in the treatment of inflammatory diseases, such as inflammatory bowl disorder (IBD), asthma, allergic and atopic reactions.

The method and compositions of the present invention are further useful for modulating the immune response in a subject disposed of an autoimmune disease. In addition, suppression of an immune response according to the method of the present invention can be useful for the development and implementation of immunological diagnostic and research tools and assays.

Incubation of Expression Vector with PBMC

In an alternate embodiment of the present invention, the expression sequences for cytolethal distending toxin (cdt), leukotoxin (ltx) and heat shock protein GroEL (cumulatively refered to herein as "Toxins") may be isolated and the expression sequence may be inserted or cloned into plasmid, phage or cosmid vectors to form recombinant molecules that may be subsequently transferred into a host cell by various means such as transformation, transduction, transfection, conjugation, etc. This is well within the skill of one in the art. The host cell carrying the expression vector may then be incubated with either whold blood or PBMC and the resulting Tr1 cells may be isolated and administered as discussed previously. Again, other proteins such as, but not limited to Interleukin-10 may be co-incubated. It may also be desireable to incubate fragments of *A. actinomycetemcomitans* such as lipopolysaccharide (LPS) into the innoculum.

Incubation of Toxins with PBMC

Alternatively the host cells containing the expression vector discussed above may be cultured and the expressed proteins isolated and purified. The purified proteins may then be added directly to the whole blood or PBMC in comination with or without other proteins such as, but not limited to Interleukin-10 and fragments of *A. actinomycetemcomitans* such as lipopolysaccharide (LPS) into the innoculum. The resulting Tr1 cells may be isolated and administered as discussed previously.

In Vivo Manipulation

In an alternate embodiment inducing differentiation and promoting proliferation of regulatory T cells can be achieved in vivo by administering directly to a patient in need of immune sytem modulation at least three proteins, cytolethal distending toxin (cdt), leukotoxin (ltx) and a heat shock protein, such as GroEL (referred to cumulatively as “Toxins”). These three proteins can be introduced in the form of a subunit vaccine or a whole organism vaccine wherein the attenuated pathogenic organism, is *A. actinomycetemcomitans*; alternatively, the expression sequences for these proteins may be cloned into an expression vector and expressed directly within the patient.

Vaccines

In general, active vaccines can be divided into two general classes: subunit vaccines and whole organism vaccines. Subunit vaccines, are prepared from components of the whole organism and are usually developed in order to avoid the use of live organisms that may cause disease or to avoid the toxic components present in whole organism vaccines, as discussed in further detail below. The use of purified capsular polysaccharide material of *H. influenza* type b, as a vaccine against the meningitis caused by this organism in humans, is an example of a vaccine based upon an antigenic component. See Parks, et al., *J. Inf. Dis*., 136 (Suppl.):551 (1977), Anderson, et al., *J. Inf. Dis*., 136 (Suppl.):563 (1977); and Makela, et al., *J. Inf. Dis*., 136 (Suppl.):543 (1977).

Subunit Vaccines

As discussed previously, the cytolethal distending toxin (cdt), leukotoxin (ltx) and GroEL proteins or homologs thereof can be obtained in a purified form. In the present embodiment these proteins or Toxins may then be combined with a delivery vehicle and administered directly to the patient in need of immune system modulation. Alternativey, the expression vector(s) containg the cloned expression sequences may be combined with a delivery vehicle and administered directly to the patient in need of immune system modulation.

More particularly, the genetic immunization method of the present invention comprises the suppression of an immune response in a mammal by intravenous or intraperitoneal administration (i.e., systemic administration) of a therapeutic composition which includes cdt, ltx and/or GroEl complexed with a delivery vehicle; or alternatively an expression plasmid capable of expressing cdt, ltx and/or GroEL complexed with a delivery vehicle.

According to the present invention, the delivery vehicle comprises a lipid composition that is capable of fusing with the plasma membrane of a cell, thereby allowing the liposome to deliver Toxin(s) and/or an expression plasmid into a cell. A liposome is also capable of either incorporating an immunogen on its surface or incorporating the immunogen internally. Suitable delivery vehicles for use with the present invention include any liposome. Some preferred liposomes of the present invention include those liposomes commonly used in, for example, gene delivery methods known to those of skill in the art. Some preferred delivery vehicles comprise multilamellar vesicle (MLV) lipids and extruded lipids, although the invention is not limited to such liposomes.

Methods for preparation of MLV’s are well known in the art and are described, for example, in U.S. Pat. No. 6,693,086, which is incorporated herein by reference. According to the present invention, “extruded lipids” are lipids which are prepared similarly to MLV lipids, but which are subsequently extruded through filters of decreasing size, as described in Templeton, et al., *Nature Biotech*., 15:647-652 (1997), which is incorporated herein by reference in its entirety. Small unilamellar vesicle (SUV) lipids can also be used in the composition and method of the present invention and have been shown to be effective in combination with nucleic acids for eliciting an immune response (see, U.S. Pat. No. 6,693,086). Other preferred liposome delivery vehicles comprise liposomes having a polycationic lipid composition (i.e., cationic liposomes). For example, cationic liposome compositions include, but are not limited to, any cationic liposome complexed with cholesterol, and without limitation, include DOTMA (N-[1-(2,3-dioleoxyloxy)propyl]-N,N,N-trimethyl ammonium chloride) and cholesterol, DOTAP (1,2-Dioleoyl-3-Trimethylammonium-Propane) and cholesterol, DOTIM (1-(2-(oleoyloxy)ethyl)-2-oleyl-3-(2-hydroxyethyl)imidazolinium) and cholesterol, PEI (Polyethylenimine) and cholesterol and DDAB (Dimethyldioctadecylammonium) and cholesterol.

As discussed above, a vaccine or therapeutic composition of the present invention is administered to a mammal in a manner effective to deliver the composition to a cell, a tissue, and/or systemically to the mammal, whereby suppression of an immune response is achieved as a result of the administration of the composition. It is noted that while it is possible to specifically target the therapeutic composition of the present invention to a particular cell or tissue, it is not necessary, since the inventors have found that several different modes of administration in the absence of specific targeting is effective to elicit the desired immune response. Suitable administration protocols include any in vivo or ex vivo administration protocol. According to the present invention, suitable methods of administering a vaccine or therapeutic composition of the present invention to a patient include any route of in vivo administration that is suitable for delivering the composition into a patient. The preferred routes of administration will be apparent to those of skill in the art, depending on the type of condition to be prevented or treated, and/or the target cell population. Preferred methods of in vivo administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, subcutaneous administration, intraarticular administration, intraventricular administration, inhalation (e.g., aerosol), intracranial, intraspinal, intraocular, intranasal, oral, bronchial, rectal, topical, vaginal, urethral, pulmonary administration, impregnation of a catheter, and direct injection into a tissue. In particular, any routes of delivery which suppress an immune response in the mucosal tissues is preferred. Such routes include bronchial, intradermal, intramuscular, intranasal, other inhalatory, rectal, subcutaneous, topical, transdermal, vaginal and urethral routes. Some particularly preferred routes of administration include, intravenous, intraperitoneal, subcutaneous, intradermal, intranodal, intramuscular, transdermal, inhaled, intranasal, rectal, vaginal, urethral, topical, oral, intraocular, intraarticular, intracranial, and intraspinal. As discussed previously, combinations of routes of delivery can be used and in some instances, may enhance the therapeutic effects of the vaccine or composition. Therefore, any combination of two or more routes of administration, performed simultaneously, within a short time period one after another, or at different time intervals relative to the immunization schedule (e.g., initial administration versus boosters), are contemplated by the present inventors. In one embodiment, a preferred route of administration is a combination of any one or more of intravenous, intraperitoneal or intradermal administration with intranodal administration. In another embodiment where the target cells are in or near a tumor, a preferred route of administration is by direct injection into the tumor or tissue surrounding the tumor.

Ex vivo administration refers to performing part of the regulatory step outside of the patient, such as administering a composition of the present invention to a population of cells removed from a patient under conditions such that the composition contacts and/or enters the cell, and returning the lipofected cells to the patient. Ex vivo methods are particularly suitable when the target cell can easily be removed from and returned to the patient.

When the route of administration is intravenous, the primary site of immunization (i.e., suppression of an immune response) is the lung, which is a very active organ immunologically, containing large numbers of both effector cells (e.g., T cells, B cells, NK cells) and antigen presenting cells (e.g., macrophages, dendritic cells). Similarly, when the route of administration is intraperitoneal, the primary sites of immunization are the spleen and liver, both of which are also immunologically active organs.

Suppression of an immune response in a mammal can be an effective treatment for a wide variety of medical disorders, and in particular, an autoimmune disease, transplant rejection and cancer. According to the present invention, "suppressing an immune response" in a mammal refers to specifically controlling or influencing the activity of the immune response, and can include altering an immune response (such as by eliciting a type of immune response which in turn changes the prevalent type of immune response in a mammal from one which is harmful or ineffective to one which is beneficial or protective) and/or down suppressing an immune response.

One component of the therapeutic composition used in the present method is a protein or alternatively a nucleic acid sequence, which includes coding and/or non-coding nucleic acid sequences. As used herein, a "coding" nucleic acid sequence refers to a nucleic acid sequence which encodes at least a portion of a peptide or protein (e.g. a portion of an open reading frame), and can more particularly refer to a nucleic acid sequence encoding a peptide or protein which is operatively linked to a transcription control sequence, so that the peptide or protein can be expressed. A "non-coding" nucleic acid sequence refers to a nucleic acid sequence which does not encode any portion of a peptide or protein. According to the present invention, "non-coding" nucleic acids can include regulatory regions of a transcription unit, such as a promoter region. The term, "empty vector" can be used interchangeably with the term "non-coding", and particularly refers to a nucleic acid sequence in the absence of a peptide or protein coding portion, such as a plasmid vector without a gene insert. The phrase "operatively linked" refers to linking a nucleic acid molecule to a transcription control sequence in a manner such that the molecule is capable of expression when transfected (i.e., transformed, transduced or transfected) into a host cell. Therefore, a nucleic acid sequence that is "not operatively linked to a transcription control sequence" refers to any nucleic acid sequence, including both coding and non-coding nucleic acid sequences, which are not linked to a transcription control sequence in a manner such that the molecule is capable of expression when transfected into a host cell. It is noted that this phrase does not preclude the presence of a transcription control sequence in the nucleic acid molecule.

In some embodiments of the present invention, a nucleic acid sequence included in a therapeutic composition of the present invention is incorporated into a recombinant nucleic acid molecule, and encodes an immunogen and/or a cytokine. As discussed in detail below, preferred immunogens include a tumor antigen, an allergen or an antigen from an infectious disease pathogen (i.e., a pathogen antigen). The phrase "recombinant molecule" primarily refers to a nucleic acid molecule or nucleic acid sequence operatively linked to a transcription control sequence, but can be used interchangeably with the phrase "nucleic acid molecule" which is administered to a mammal.

According to the present invention, an isolated, or biologically pure, nucleic acid molecule or nucleic acid sequence, is a nucleic acid molecule or sequence that has been removed from its natural milieu. As such, "isolated" and "biologically pure" do not necessarily reflect the extent to which the nucleic acid molecule has been purified. An isolated nucleic acid molecule useful in the present composition can include the coding region for cytolethal distending toxin (cdt), leukotoxin (ltx) and a heat shock protein, such as GroEL and/or homologs thereof.

Transcription control sequences are sequences that control the initiation, elongation, and termination of transcription. Particularly important transcription control sequences are those that control transcription initiation, such as promoter, enhancer, operator and repressor sequences. Suitable transcription control sequences include any transcription control sequence that can function in at least one of the recombinant cells useful in the method of the present invention. A variety of such transcription control sequences are known to those skilled in the art. Preferred transcription control sequences include those that function in mammalian, bacteria, insect cells, and preferably in mammalian cells. More preferred transcription control sequences include, but are not limited to, simian virus 40 (SV-40), β-actin, retroviral long terminal repeat (LTR), Rous sarcoma virus (RSV), cytomegalovirus (CMV), tac, lac, trp, trc, oxy-pro, omp/lpp, rrnB, bacteriophage lambda (λ) (such as λpL and λpR and fusions that include such promoters), bacteriophage T7, T7lac, bacteriophage T3, bacteriophage SP6, bacteriophage SP01, metallothionein, alpha mating factor, *Pichia* alcohol oxidase, alphavirus subgenomic promoters (such as Sindbis virus subgenomic promoters), baculovirus, *Heliothis zea* insect virus, vaccinia virus and other poxviruses, herpesvirus, and adenovirus transcription control sequences, as well as other sequences capable of controlling gene expression in eukaryotic cells. Additional suitable transcription control sequences include tissue-specific promoters and enhancers (e.g., T cell-specific enhancers and promoters). Transcription control sequences of the present invention can also include naturally occurring transcription control sequences naturally associated with a gene encoding an immunogen, including tumor antigen, an allergen, a pathogen antigen or a cytokine.

Particularly preferred transcription control sequences for use in the present invention include promoters that allow for transient expression of a nucleic acid molecule that is to be expressed, thereby allowing for expression of the protein encoded by the nucleic acid molecule to be terminated after a time sufficient to suppress an immune response. Adverse effects related to prolonged activation of the immune system can be avoided by selection of promoters and other transcription control factors that allow for transient expression of a nucleic acid molecule. This is yet another point of difference between the method of the present invention and previously described gene therapy/gene replacement protocols. Suitable promoters for use with nucleic acid molecules encoding immunogens and/or cytokines for use in the present invention include cytomegalovirus (CMV) promoter and other non-retroviral virus-based promoters such as RSV promoters, adenovirus promoters and Simian virus promoters. LTR, tissue-specific promoters, promoters from self-replication viruses and papillomavirus promoters, which may be quite desirable in gene therapy/gene replacement protocols because they provide prolonged expression of a transgene, are not preferred transcription control sequences for use in the present invention.

Recombinant molecules of the present invention, which can be either DNA or RNA, can also contain additional regulatory sequences, such as translation regulatory sequences, origins of replication, and other regulatory sequences that are compatible with the recombinant cell. In one embodiment, a recombinant molecule of the present invention also contains secretory signals (i.e., signal segment nucleic acid sequences) to enable an expressed toxin or cytokine protein to be secreted from the cell that produces the protein. Suitable signal segments include: (1) an immunogen signal segment (e.g., a tumor antigen, allergen or pathogen antigen signal segment); (2) a cytokine signal segment; (3) or any heterologous signal segment capable of directing the secretion of a toxin and/or cytokine protein according to the present invention.

Preferred recombinant molecules of the present invention include a recombinant molecule containing a nucleic acid sequence encoding an immunogen, a recombinant molecule containing a nucleic acid sequence encoding a cytokine, or a recombinant molecule containing both a nucleic acid sequence encoding a toxin and a nucleic acid sequence encoding a cytokine to form a chimeric recombinant molecule (i.e., the nucleic acid sequence encoding the immunogen and the nucleic acid sequence encoding the cytokine are in the same recombinant molecule). The nucleic acid molecules contained in such recombinant chimeric molecules are operatively linked to one or more transcription control sequences, in which each nucleic acid molecule contained in a chimeric recombinant molecule can be expressed using the same or different transcription control sequences.

One or more recombinant molecules of the present invention can be used to produce an encoded product (i.e., a toxin or a cytokine protein) useful in the method of the present invention. In one embodiment, an encoded product is produced by expressing a nucleic acid molecule as described herein under conditions effective to produce the protein. A preferred method to produce an encoded protein is by transfecting a host cell with one or more recombinant molecules to form a recombinant cell. Suitable host cells to transfect include any mammalian cell that can be transfected. Host cells can be either untransfected cells or cells that are already transformed with at least one nucleic acid molecule. Host cells according to the present invention can be any cell capable of producing a toxin (e.g., cytolethal distending toxin (cdt), leukotoxin (ltx) and a heat shock protein, such as GroEL) and/or a cytokine according to the present invention. A preferred host cell includes a mammalian lung cells, lymphocytes, muscle cells, hematopoietic precursor cells, mast cells, natural killer cells, macrophages, monocytes, epithelial cells, endothelial cells, dendritic cells, mesenchymal cells, Langerhans cells, cells found in granulomas and tumor cells of any cellular origin. An even more preferred host cell of the present invention includes mammalian mesenchymal cells, epithelial cells, endothelial cells, macrophages, monocytes, lung cells, muscle cells, T cells and dendritic cells.

According to the method of the present invention, a host cell is preferably transfected in vivo (i.e., in a mammal) as a result of intravenous or intraperitoneal administration to a mammal of a nucleic acid molecule complexed to a liposome delivery vehicle. Transfection of a nucleic acid molecule into a host cell according to the present invention can be accomplished by any method by which a nucleic acid molecule administered with a liposome delivery vehicle can be inserted into the cell in vivo, and includes lipofection.

It may be appreciated by one skilled in the art that use of recombinant DNA technologies may improve expression of transfected nucleic acid molecules by manipulating, for example, the duration of expression of the transgene (i.e., recombinant nucleic acid molecule), the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, increasing the duration of expression of the recombinant molecule, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, and deletion of sequences that destabilize transcripts.

One embodiment of the method of the present invention, when the mammal has an autoimmune disease, a therapeutic composition to be intravenously administered to the mammal comprises a plurality of recombinant nucleic acid molecules, wherein each of the recombinant nucleic acid molecules comprises a cDNA sequence, each of the cDNA sequences encoding a toxin, such as cdt and ltx or a fragment thereof or a heat shock protein or fragment thereof. Each of the plurality of cDNA sequences is operatively linked to a transcription control sequence. Administration of such a therapeutic composition to a mammal that has an autoimmune disease results in the expression of the cDNA sequences encoding the toxins in the tissue of the mammal (pulmonary tissue by intravenous administration and spleen and liver by intraperitoneal administration). In a further embodiment, such a therapeutic composition comprises a recombinant nucleic acid molecule having a nucleic acid sequence encoding a cytokine, wherein the nucleic acid sequence is operatively linked to a transcription control sequence. Administration of such a therapeutic composition to a mammal results in the expression of the nucleic acid sequence encoding the cytokine in the above-mentioned tissues of the mammal.

In yet another embodiment of the present invention of the method to suppress an immune response in a mammal that has recently received an organ transplant, a therapeutic composition to be intravenously or intraperitoneally administered to a mammal comprises a plurality of recombinant nucleic acid molecules, wherein each of the recombinant nucleic acid molecules comprises a cDNA sequence, each of the cDNA sequences encoding a toxin or a fragment thereof. Each of the plurality of cDNA sequences is operatively linked to a transcription control sequence. Administration of such a therapeutic composition to a mammal that has recently received an organ transplant results in the expression of the cDNA sequences encoding the toxins in the tissue of the mammal (according to the route of administration, as previously discussed). In a further embodiment, such a therapeutic composition comprises a recombinant nucleic acid molecule having a nucleic acid sequence encoding a cytokine, wherein the nucleic acid sequence is operatively linked to a transcription control sequence. Administration of such a therapeutic composition to a mammal results in the expression of the nucleic acid sequence encoding the cytokine in the tissues of the mammal.

In yet another embodiment of the present invention of the method to suppress an immune response in a mammal, a therapeutic composition to be intravenously or intraperitoneally administered to a mammal comprises a plurality of recombinant nucleic acid molecules, each of the recombinant nucleic acid molecules comprising a cDNA sequence amplified from total RNA isolated from at least one toxin. In this embodiment, the cDNA sequences are amplified from total RNA, or a fragment thereof, that has been isolated from at least one, and preferably, multiple, toxins. Each of the plurality of cDNA sequences is operatively linked to a transcription control sequence. Administration of such a therapeutic composition to a mammal that has or might contract a disease associated with allergic inflammation results in the expression of the cDNA sequences encoding the toxins in the tissue of the mammal (according to the route of administration, as previously discussed). In a further embodiment, such a therapeutic composition comprises a recombinant nucleic acid molecule having a nucleic acid sequence encoding a cytokine, wherein the nucleic acid sequence is operatively linked to a transcription control sequence. Administration of such a therapeutic composition to a mammal results in the expression of the nucleic acid sequence encoding the cytokine in the tissues of the mammal.

A therapeutic composition of the present invention includes a liposome delivery vehicle. According to the present invention, a liposome delivery vehicle comprises a lipid composition that is capable of preferentially delivering a therapeutic composition of the present invention to the pulmonary tissues in a mammal when administration is intravenous, and to the spleen and liver tissues of a mammal when administration is intraperitoneal. The phrase "preferentially delivering" means that although the liposome can deliver a nucleic acid molecule to sites other than the pulmonary or spleen and liver tissue of the mammal, these tissues are the primary site of delivery.

A liposome delivery vehicle of the present invention can be modified to target a particular site in a mammal, thereby targeting and making use of a toxin and/or a nucleic acid molecule of the present invention at that site. Suitable modifications include manipulating the chemical formula of the lipid portion of the delivery vehicle. Manipulating the chemical formula of the lipid portion of the delivery vehicle can elicit the extracellular or intracellular targeting of the delivery vehicle. For example, a chemical can be added to the lipid formula of a liposome that alters the charge of the lipid bilayer of the liposome so that the liposome fuses with particular cells having particular charge characteristics. Other targeting mechanisms, such as targeting by addition of exogenous targeting molecules to a liposome (i.e., antibodies) are not a necessary component (but may be an optional component) of the liposome delivery vehicle of the present invention, since effective immune suppression at immunologically active organs is already provided by the composition and route of delivery of the present compositions without the aid of additional targeting mechanisms. Additionally, for efficacy, the present invention does not require that a protein encoded by a given nucleic acid molecule be expressed within the target cell (e.g., tumor cell, pathogen, etc.). The compositions and method of the present invention are efficacious when the proteins are expressed in the vicinity of (i.e., adjacent to) the target site, including when the proteins are expressed by non-target cells.

A liposome delivery vehicle is preferably capable of remaining stable in a mammal for a sufficient amount of time to deliver the toxins and/or cytokines and/or a nucleic acid molecule of the present invention to a preferred site in the mammal. A liposome delivery vehicle of the present invention is preferably stable in the mammal into which it has been administered for at least about 30 minutes, more preferably for at least about 1 hour and even more preferably for at least about 24 hours.

A liposome delivery vehicle of the present invention comprises a lipid composition that is capable of fusing with the plasma membrane of the targeted cell to deliver a toxin and if desired a nucleic acid molecule into a cell. Preferably, when a toxin:liposome complex of the present invention is administered intravenously, the transfection efficiency of the toxin:liposome complex of the present invention is at least about 1 picogram (pg) of protein expressed per milligram (mg) of total tissue protein per microgram ($\mu$g) of nucleic acid delivered. More preferably, the transfection efficiency of a toxin:liposome complex of the present invention is at least about 10 pg of protein expressed per mg of total tissue protein per $\mu$g of nucleic acid delivered; and even more preferably, at least about 50 pg of protein expressed per mg of total tissue protein per $\mu$g of nucleic acid delivered; and most preferably, at least about 100 pg of protein expressed per mg of total tissue protein per $\mu$g of nucleic acid delivered. When the route of delivery of a toxin:lipid complex of the present invention is intraperitoneal, the transfection efficiency of the complex can be as low as 1 fg of protein expressed per mg of total tissue protein per $\mu$g of nucleic acid delivered, with the above amounts being more preferred.

A preferred liposome delivery vehicle of the present invention is between about 100 and 500 nanometers (nm), more preferably between about 150 and 450 nm and even more preferably between about 200 and 400 nm in diameter.

According to the present invention, an effective administration protocol (i.e., administering a therapeutic composition in an effective manner) comprises suitable dose parameters and modes of administration that result in elicitation of an immune response in a mammal that has a disease, preferably so that the mammal is protected from the disease. Effective dose parameters can be determined using methods standard in the art for a particular disease. Such methods include, for example, determination of survival rates, side effects (i.e., toxicity) and progression or regression of disease. In particular, the effectiveness of dose parameters of a therapeutic composition of the present invention when treating an autoimmune disease can be determined by assessing response rates. Such response rates refer to the percentage of treated patients in a population of patients that respond with either partial or complete remission. Remission can be determined by, for example, measuring white blood cell count.

In accordance with the present invention, a suitable single dose size is a dose that is capable of suppressing an immune response in a mammal with a disease when administered one or more times over a suitable time period. Doses can vary depending upon the disease being treated. Doses of a therapeutic composition of the present invention suitable for use with intravenous or intraperitoneal administration techniques can be used by one of skill in the art to determine appropriate single dose sizes for systemic administration based on the size of a mammal.

In a preferred embodiment, an appropriate single dose of a toxin:liposome or toxin:nucleic acid:liposome complex of the present invention is from about 0.1 µg to about 100 µg per kg body weight of the mammal to which the complex is being administered. In another embodiment, an appropriate single dose is from about 1 μg to about 10 μg per kg body weight. In another embodiment, an appropriate single dose of toxin: lipid complex is at least about 0.1 μg of toxin to the mammal, more preferably at least about 1 μg of toxin, even more preferably at least about 10 μg of toxin, even more preferably at least about 50 μg of toxin, and even more preferably at least about 100 μg of toxin to the mammal.

Preferably, when nucleic acid:liposome complexes of the present invention contains a nucleic acid molecule which is to be expressed in the mammal, an appropriate single dose of a nucleic acid:liposome complex of the present invention results in at least about 1 pg of protein expressed per mg of total tissue protein per μg of nucleic acid delivered. More preferably, an appropriate single dose of a nucleic acid:liposome complex of the present invention is a dose which results in at least about 10 pg of protein expressed per mg of total tissue protein per μg of nucleic acid delivered; and even more preferably, at least about 50 pg of protein expressed per mg of total tissue protein per μg of nucleic acid delivered; and most preferably, at least about 100 pg of protein expressed per mg of total tissue protein per μg of nucleic acid delivered. When the route of delivery of a toxin:lipid complex of the present invention is intraperitoneal, an appropriate single dose of a toxin:liposome complex of the present invention is a dose which results in as low as 1 fg of protein expressed per mg of total tissue protein per μg of toxin delivered, with the above amounts being more preferred.

A suitable single dose of a therapeutic composition of the present invention to elicit a systemic, non-antigen-specific immune response in a mammal is a sufficient amount of a nucleic acid molecule complexed to a liposome delivery vehicle, when administered intravenously or intraperitoneally, to elicit a cellular and/or humoral immune response in vivo in a mammal, as compared to a mammal which has not been administered with the therapeutic composition of the present invention (i.e., a control mammal). Preferred dosages of nucleic acid molecules to be included in a nucleic acid:lipid complex of the present invention have been discussed above.

According to the present invention, a single dose of a therapeutic composition useful to suppress an immune response against an autoimmune disease comprising a pathogen-encoding recombinant molecule combined with liposomes, alone or in combination with a cytokine-encoding recombinant molecule with liposomes, is substantially similar to those doses used to treat a transplant rejection.

It will be obvious to one of skill in the art that the number of doses administered to a mammal is dependent upon the extent of the disease and the response of an individual patient to the treatment. Thus, it is within the scope of the present invention that a suitable number of doses includes any number required to treat a given disease.

In the method of the present invention, therapeutic compositions can be administered to any member of the Vertebrate class, Mammalia, including, without limitation, primates, rodents, livestock and domestic pets. Livestock include mammals to be consumed or that produce useful products (e.g., sheep for wool production). Preferred mammals to protect include humans, dogs, cats, mice, rats, sheep, cattle, horses and pigs, with humans and dogs being particularly preferred, and humans being most preferred. While a therapeutic composition of the present invention is effective to suppress an immune response against a disease in inbred species of mammals, the composition is particularly useful for eliciting an immune response in outbred species of mammals.

In another embodiment of the present invention, the therapeutic composition of the present invention as described herein at therapeutically effective concentrations or dosages may be combined with a pharmaceutically or pharmacologically acceptable carrier, excipient or diluent, either biodegradable or non-biodegradable. As used herein, a pharmaceutically acceptable excipient refers to any substance suitable for delivering a therapeutic composition useful in the method of the present invention to a suitable in vivo site. Preferred pharmaceutically acceptable excipients are capable of maintaining a toxin and/or nucleic acid molecule of the present invention in a form that, upon arrival of the toxin and/or nucleic acid molecule to a cell, the toxin and/or nucleic acid molecule is capable of entering the cell and/or being expressed by the cell if the nucleic acid molecule encodes a protein to be expressed. Suitable excipients of the present invention include excipients or formularies that transport, but do not specifically target a toxin and/or nucleic acid molecule to a cell (also referred to herein as non-targeting carriers). Standard excipients include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, polyvinylpyrrolidone, sugars and starches. Exemplary examples of carriers include, but are by no means limited to, water, phosphate buffered saline, Ringer's solution, dextrose solution, serum-containing solutions, Hank's solution, other aqueous physiologically balanced solutions, oils, esters, poly(ethylene-vinyl acetate), copolymers of lactic acid and glycolic acid, poly(lactic acid), gelatin, collagen matrices, polysaccharides, poly(D,L lactide), poly(malic acid), poly(caprolactone), celluloses, albumin, starch, casein, dextran, polyesters, ethanol, mathacrylate, polyurethane, polyethylene, vinyl polymers, glycols, mixtures thereof and the like. Aqueous carriers can contain suitable auxiliary substances required to approximate the physiological conditions of the recipient, for example, by enhancing chemical stability and isotonicity. Particularly preferred excipients include non-ionic diluents, with a preferred non-ionic buffer being 5% dextrose in water (DW5). See, for example, Remington: The Science and Practice of Pharmacy, 2000, Gennaro, A R ed., Eaton, Pa.: Mack Publishing Co.

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- or o-cresol, formalin and benzol alcohol. Therapeutic compositions of the present invention can be sterilized by conventional methods and/or lyophilized.

The invention provides kits for carrying out the methods of the invention. Accordingly, a variety of kits are provided. The kits may be used for any one or more of the following (and, accordingly, may contain instructions for any one or more of the following uses): use for therapeutically or prophylactially treating an individual following an organ transplantation; preventing an autoimmune disease; or preventing the spread or metastasis of some forms of cancer; preventing one or more symptoms of some autoimmune diseases; reducing severity of one or more symptoms associated with autoimmune diseases; or delaying development of cancer in an individual.

The kits of the invention comprise one or more containers comprising the therapeutic composition of the present invention and a suitable excipient as described herein and a set of instructions, generally written instructions although electronic storage media (e.g., magnetic diskette or optical disk) containing instructions are also acceptable, relating to the use and dosage of the therapeutic composition of the present invention for the intended treatment. The instructions included with the kit generally include information as to dosage, dosing schedule, and route of administration for the intended treatment. The containers of the therapeutic composition of the present invention may be unit doses, bulk packages (e.g., multi-dose packages) or sub-unit doses.

The therapeutic composition of the present invention may be packaged in any convenient, appropriate packaging.

As will be appreciated by one knowledgeable in the art, the therapeutic composition of the present invention may be combined or used in combination with other treatments known in the art.

Whole Organism Vaccines

Whole organism vaccines, on the other hand, make use of the entire organism for vaccination. The organism may be killed or alive (usually attenuated) depending upon the desired outcome. The present invention utilizes live attenuated vaccines or dead vaccines that are supplemented with cytotoxins.

To develop a live vaccine specific mutations may be introduced into the genome of the pathogen to be used taking care not to disrupt the cdt, ltx or GroEL genes. There are a number of well known techniques which can be employed for disabling or mutating genes, such as the employment of translocatable elements, mutagenic agents, transducing phages, and DNA-mediated transformation, and/or conjugation. Other methods also known to one with ordinary skill in the art such as recombinant DNA technology may also be employed to successively introduce one or more mutated genes into a single host strain to be used as the vaccine.

In accordance with the subject invention, vaccines are produced by introducing a non-reverting mutation into at least two genes, where each mutation is large enough to insure a substantially zero probability of reversion and assurance of the non-expression of each mutated gene. The type of genes chosen to produce the vaccine will result from non-reverting mutations in genes that will attenuate the organism but not effect the expression of cytolethal distending toxin (cdt), leukotoxin (ltx) and a heat shock protein, such as GroEL.

In an alternate embodiment live vaccines prepared in accordance with the present invention may be used as vectors or carriers for antigens of species other than the non-virulent pathogenic vaccine. One or more structural genes coding for the desired antigens may be introduced into the non-virulent pathogenic vaccine as an expression cassettes. The expression cassette comprises the structural gene or genes of interest under the regulatory control of the transcriptional and translational initiation and termination regions which naturally border the structural gene of interest. Where bacterial or bacteriophage structural genes are involved, the natural or wild-type regulatory regions will usually, but not always, suffice. It may be necessary to join regulatory regions recognized by the non-virulent pathogen to structural genes for antigens isolated from eukaryotes and occasionally prokaryotes.

The expression cassette may be a construct or may be or form part of a naturally occurring plasmid. If the expression cassette is a construct, it may be joined to a replication system for episomal maintenance or it may be introduced into the non-virulent pathogenic microorganism under conditions for recombination and integration into the non-virulent pathogen's chromosomal DNA. Structural genes for antigens of interest may encode bacterial proteins such as toxin subunits, viral proteins such as capsids, or enyzme pathways such as those involved in synthesis of carbohydrate antigens such as lipopolysaccharide (LPS). The construct or vector may be introduced into the host strain through a number of well known methods, such as, transduction, conjugation, transformation, electroporation, transfection, etc.

In an alternate embodiment, live vaccines prepared in accordance with the preferred embodiment which have non-reverting mutations in genes under nitrogen control may be used as vectors or carriers for antigens of species other than the non-virulent pathogenic vaccine. One or more structural genes coding for the desired antigens may be operatively linked to an ntr-regulated promoter. As the non-virulent pathogenic microbe senses a nitrogen deficiency, expression of the ntr genes increases accordingly, thus initiating expression of genes transcribed from ntr promoters. For example, one or more structural genes coding for the desired antigens may be operatively linked to the glnAp2 promoter located on a suicide vector or an autonomously replicating plasmid. The suicide vector or plasmid may then be introduced into the non-virulent pathogenic strain having non-reverting mutations by well known methods, such as, transduction, transformation, electroporation, tri-parental mating techniques or direct transfer of a self mobilized vector in a bi-parental mating and maintained within the microorganism either autonomously or in the bacterial host's chromosomal DNA.

The invention is further illustrated by the following non-limited examples. All scientific and technical terms have the meanings as understood by one with ordinary skill in the art. The specific examples which follow illustrate the methods in which the compositions of the present invention may be prepared and are not to be construed as limiting the invention in sphere or scope. The methods may be adapted to variation in order to produce compositions embraced by this invention but not specifically disclosed. Further, variations of the methods to produce the same compositions in somewhat different fashion will be evident to one skilled in the art.

EXAMPLES

The examples herein are meant to exemplify the various aspects of carrying out the invention and are not intended to limit the invention in any way.

Materials and Methods

Subjects. 25 systemically and periodontally healthy subjects participated in this study. Subjects included 15 males and 10 females with a mean age of 35 years. Subjects were requested to sign an informed consent that was previously approved by the Institutional Review Board at the University of Southern California. Cultural analysis was used to select subjects for this study that did not harbor *A. actinomycetemcomitans* in their dental plaque. This entailed sampling of the dental plaque from 3 periodontal sulcus sites for each patient using paper points. The plaque samples were then inoculated on TSBV selective media and cultivable colonies were examined for the presence of *A. actinomycetemcomitans* (Slots, J., *J. Clin. Microbiol.*, 15:606 (1982)). The rationale for selecting *A. actinomycetemcomitans* culture-negative subjects was to exclude subjects, whose T cell repertoire had potentially been altered during the course of a chronic infection with *A. actinomycetemcomitans*.

Isolation of Peripheral Blood Mononuclear Cells (PBMC). Venous blood was drawn from healthy volunteers. Peripheral blood mononuclear cells were isolated by Ficoll-Hypaque density gradient centrifugation (Böyum, A., *Scandinavian Journal Of Clinical And Laboratory Investigation. Supplement*, 97:77 (1968)).

Bacteria. A spontaneously occurring non-fimbriated mutant, designated as strain D7S-smooth, which was derived from a clinical *A. actinomycetemcomitans* isolate (strain D7S) was used in this study, as the wild type (WT) parent strain. Strain D7S was originally recovered from a patient with aggressive periodontitis. WT and isogenic mutants with specific deletions in the ltx and cdtABC genes, designated as Δltx and ΔcdtABC strains, respectively, were provided by Dr. Casey Chen of the University of Southern California (Nalbant, A., et al., *Oral Microbiology and Immunology*, 15:290 (2000).) *A. actinomycetemcomitans* bacteria were grown and their antigenic preparations were prepared as previously described (Nalbant, A., et al., *Oral Microbiology and Immunology*, 15:290 (2000)).

PBMC Stimulants. The stimulatory agents used in these studies included varying concentrations of *A. actinomycetemcomitans* antigenic preparation (0-100 µg/ml), PHA (0-50 µg/ml), SEE (0-0.5 µg/ml) and phorbol 12-myristate 13-acetate (PMA, 25 ng/ml) in conjunction with ionomycin (1 µg/ml).

Stimulation of Mononuclear Cells. PBMC were placed in 12×75 mm culture tubes at a concentration of $2\times10^6$ cells/ml and total culture volume of 10 ml. The cells were cultured in the presence or absence of stimulants for various intervals in a humidified incubator at 37° C. and 5% $CO_2$. The medium consisted of RPMI-1640 supplemented with 10% FBS and penicillin (100 units/ml)/streptomycin (100 µg/ml) and 25 mM HEPES buffer. For flow cytometric detection of cytokines, Brefeldin-A (BFA, 10 µg/ml) was included during the last 4 hours of culture to prevent secretion of cytokines and retain them intracellularly.

Co-Culture Studies. PBMC were pre-stimulated by incubation in the presence or absence of *A. actinomycetemcomitans* antigenic preparation for 48 hours. Cultured cells were harvested, washed and in some studies further separated into $CD4^+CD25^+$ and $CD4^+CD25^-$ subsets. PBMC pre-stimulated with *A. actinomycetemcomitans* antigenic preparation or its various subsets were co-cultured at different ratios with autologous freshly-isolated PBMC. These secondary cultures were re-stimulated with PMA and ionomycin for 4 hours, followed by determination of cytokine expression by intracellular staining assays.

Cytokine ELISA Assay. Quantification of IL-2, IL-10, IL-12 and IFN-γ were accomplished using a matched pair ELISA (Endogen Inc., Cambridge, Mass.). Measurement of cytokine expression by PBMC was conducted on supernatants taken from cultures subjected to various conditions of stimulation and duration of culture. Briefly, 96-well assay plates were treated for 12 hours with 3 µg/ml mouse anti-human IFN-γ or IL-10 monoclonal antibodies (Endogen Inc., Cambridge, Mass.), followed by 2-hour incubation with 50 µl of PBMC culture supernatant. Assay plates were then incubated with biotinylated mouse anti-human cytokine monoclonal detecting antibody at 0.1 to 0.5 µg/ml and linked to horseradish peroxidase-conjugated streptavidin (Zymed Laboratories Inc., San Francisco, Calif.). Assay plates were incubated with tetramethylbenzidine (TMB) substrate (Dako Inc., Carpenteria, Calif.). Concentrations of cytokines in each sample supernatant were estimated by spectrophotometric detection of cytokine-bound antibodies at 450 nm, using a BioRad 2550 microtiter plate reader. For conversion of optical density values to IFN-γ and IL-12 concentrations, the lower limits of sensitivity were considered to be 25 pg/ml and 5.0 pg/ml, respectively.

Immunofluorescence. Direct 3-color immunofluorescence assays of single cells in suspensions were performed, as previously described (Nalbant, A., et al., *Oral Microbiology and Immunology*, 15:290 (2000)). Briefly, $10^6$ cells were incubated with a mixture of fluorochrome-conjugated monoclonal antibodies for 20 min at 4° C. The cells were then washed twice and fixed with 2% buffered paraformaldehyde and analyzed by flow cytometry.

Intracellular Cytokine Detection Assay by Flow Cytometry. Cultured cells were harvested and intracellular expression of cytokines (IL-2, IL-4, IL-10 and IFN-γ) was detected by immunofluorescent labeling with specific monoclonal antibodies and flow cytometry, as described (Nalbant, A., et al., *Oral Microbiology and Immunology*, 15:290 (2000)). Briefly, cells were incubated for 10 min with permabilizing solution (Becton Dickinson, San Jose, Calif.) at room temperature. The cells were then washed and incubated with a mixture of fluorochrome-conjugated monoclonal antibodies in microtiter plates for 30 min at room temperature. Following two washes, the cells were fixed with 2% buffered paraformaldehyde and analyzed by flow cytometry.

IL-10 Neutralization. PBMC were stimulated with *A. actinomycetemcomitans* antigenic preparation (50 µg/ml) in the presence of 0.1 to 10 μg/ml mouse anti-human IL-10 or isotype control (nonspecific) monoclonal antibodies. Supernatants were collected after 24 hours and analyzed by ELISA for IFN-γ and IL-12.

Detection of Cytokine Profile of Apoptotic T Cells. The presence of cells with externalized phosphatidylserine (PS) as an apoptotic marker were detected with Annexin V labeling by modification of previously published method (Nalbant, A., et al., Oral Microbiology and Immunology, 15:290 (2000)). Briefly, PBMC were stimulated with A. actinomycetemcomitans antigenic preparation (25 μg/ml) or PMA (25 ng/ml) in conjunction with ionomycin (1 μg/ml) for 48 hours. Cultured cells were first labeled with a mixture of anti-CD3 monoclonal antibody and Annexin V in the presence of $Ca^{++}$ binding solution. The cells were then washed twice with cold PBS, fixed, permeabilized and labeled with anti-IFN-γ and anti-IL-10 monoclonal antibodies, as described for intracellular cytokine staining. Labeled cells were analyzed by flow cytometry. Annexin V-positive were designated as early apoptotic cells that have externalized their cell membrane PS and have an intact cell membrane.

Isolation of $CD4^+CD25^+$ Cells. PBMC were cultured with A. actinomycetemcomitans antigenic preparation as described above for 48 hours. To enrich for $CD4^+$ T cells, a negative selection scheme was used, where cultured cells were labeled with a mixture of monoclonal antibodies specific for CD8, CD14, CD16 and CD19 (Becton Dickinson, San Jose, Calif.). The cells were then washed and labeled with immunomagnetic beads conjugated with goat-anti-mouse IgG (Miltinyi Biotec, Auburn, Calif.). The immunomagnetically labeled cells were passed through a column filled with steel wires and held near the magnet (MiniMACS; Miltinyi Biotec). Non-adherent cells were collected as source of enriched $CD4^+$ T cells. To isolate $CD4^+CD25^+$ T cells, a positive selection scheme was used, where enriched $CD4^+$ T cells were labeled with anti-CD25 monoclonal antibody (Becton Dickinson, San Jose, Calif.). The cells were then washed and labeled with immunomagnetic beads conjugated with goat-anti-mouse IgG (Miltinyi Biotec), followed by passage through the column held near the magnet (VarioMACS; Miltinyi Biotec, Auburn, Calif.). The non-adherent cells were washed off as $CD25^-$ cells and the magnet was removed to elute the adherent cells, which were $CD25^+$ cells. Immunofluorescent labeling was performed and demonstrated that the isolated cells were >90% $CD25^+$.

Flow Cytometry. Immunofluorescently-labeled cells were processed on a FACSCalibur (Becton-Dickinson Immunocytometry Systems, San Jose, Calif.) flow cytometer equipped with an argon ion laser (488 nm), and the data were analyzed using CellQuest software (Becton Dickinson). The data acquired by flow cytometry were limited to the cell subsets of interest by selection of electronic gates. Lymphocyte gates were selected on the basis of their forward and side scatter profiles. T cells were identified with anti-CD3 monoclonal antibody.

Statistical Analysis. Mean and standard error of the mean (S.E.M.) of data were calculated. To test the statistical significance of differences between experimental and control treatment of cell subsets, two-tailed Student's t-test was used.

Results

Induction of Hypo-Responsiveness by Co-Culture. To test the ability of A. actinomycetemcomitans-stimulated PBMC to suppress the T cell responses, e.g., cytokine expression, co-culture experiments were conducted. Referring to FIG. 1, freshly isolated PBMC were incubated with A. actinomycetemcomitans antigenic preparation (25 μg/ml) for 48 hours. Cultured cells were harvested, washed and co-cultured at various ratios with autologous freshly isolated PBMC in the presence of PMA and ionomycin for 4 hours. Cytokine expression was measured with intracellular staining and analyzed by flow cytometry. The data are representative of five independent experiments. Mean proportion of IFN-γ positive T cells are shown.

Results from these co-culture studies revealed that stimulation of freshly-isolated PBMC with PMA and ionomycin induced a time-dependent increase in the expression of IFN-γ (FIG. 1). Maximal expression of IFN-γ was detected at 24 hours after incubation of PBMC with PMA and ionomycin, where 25% of T cells were IFN-γ$^+$. Surprisingly, when increasing numbers of PBMC pre-stimulated with A. actinomycetemcomitans antigenic preparation were added to this culture, a dose-dependent reduction of IFN-γ expression was observed. Addition of PBMC pre-stimulated with A. actinomycetemcomitans antigenic preparation at a ratio of 1:10 resulted in a 50% decline in IFN-γ expression. When PBMC pre-stimulated with A. actinomycetemcomitans antigenic preparation were included at a ratio of 1:2, merely 8% of T cells were IFN-γ$^+$.

Figure 2:
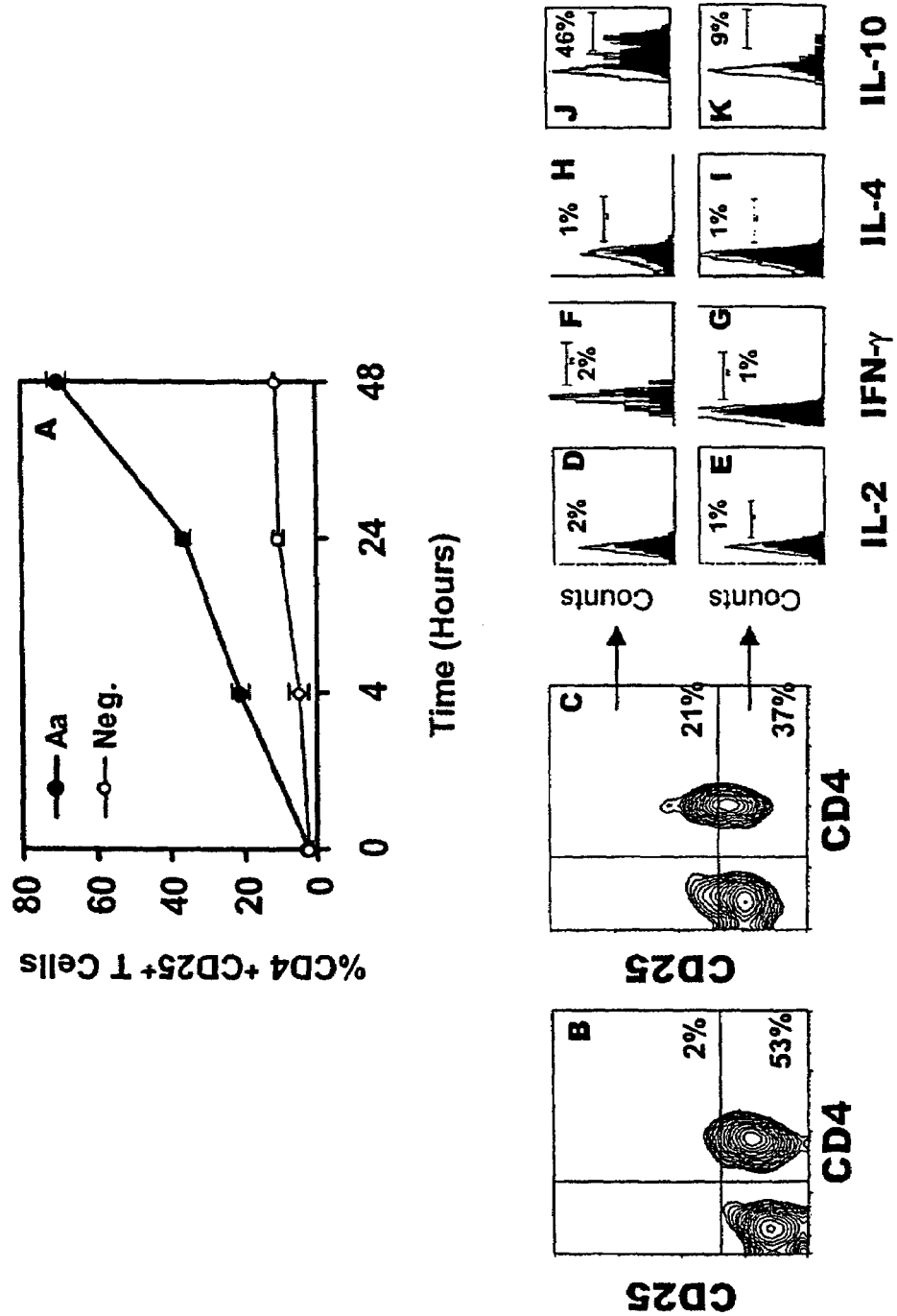
FIG. 2 shows induction and phenotypic analysis of $CD4^+$ $CD25^+$ T cells in response to *A. actinomycetemcomitans*.

$CD4^+CD25^+$ T Cells. To begin to determine whether $CD4^+CD25^+$ regulatory T cells are responsible for the suppression of the cytokine expression in response to A. actinomycetemcomitans, the proportion of $CD4^+CD25^+$ T cells following stimulation of PBMC with A. actinomycetemcomitans antigenic preparation was assessed. Referring to FIG. 2, freshly isolated PBMC were incubated with A. actinomycetemcomitans antigenic preparation (25 μg/ml) for 48 hours. Panel A: cultured cells harvested and labeled with monoclonal antibodies specific for CD25, CD3 and CD4. Labeled cells were analyzed by flow cytometry. The data are representative of five independent experiments, where the PBMC from a donor were cultured and analyzed in triplicate. Mean and S.E.M. of the proportion of $CD4^+CD25^+$ T cells are shown. The expression of cytokines was determined by the intracellular staining assay, which was conducted in concert with cell-surface labeling for the determination of CD25, CD3 and CD4 expression. Labeled cells were analyzed by flow cytometry. Representative flow cytometric profile of CD4 and CD25 expression following incubation of PBMC with media alone (Panel B) or A. actinomycetemcomitans antigenic preparation (Panel C) are shown. The expression of IL-2 (Panels D and E), IFN-γ (Panels F and G), IL-4 (Panels H and I) and IL-10 (Panels J and K) among $CD4^+CD25^+$ (Panels D, F, H and J) or $CD4^+CD25^-$ T cells (Panels E, G, I and K) is illustrated.

Results in FIG. 2A showed approximately 6% $CD4^+CD25^+$ T cells in unstimulated (negative control) PBMC cultures, compared with approximately 44% in PBMC cultures stimulated with A. actinomycetemcomitans antigenic preparation. Phenotypic analysis of $CD4^+CD25^+$ T cells was performed by intracellular cytokine staining. Results demonstrated that merely 1-2% of $CD4^+CD25^+$ T cells stimulated with A. actinomycetemcomitans antigenic preparation expressed IL-2 (FIG. 2D), IFN-γ (FIG. 2F) or IL-4 (FIG. 2H). Similarly, low expression of these cytokines was noted among the $CD4^+CD25^-$ T cell subset (FIG. 2E, G and I). Conversely, among T cells stimulated with A. actinomycetemcomitans antigenic preparation, the $CD4^+CD25^+$ subset was comprised of 46% IL-10$^+$ cells, while 9% of the $CD4^+CD25^-$ subset expressed IL-10 (FIG. 2J and K).

Figure 3:
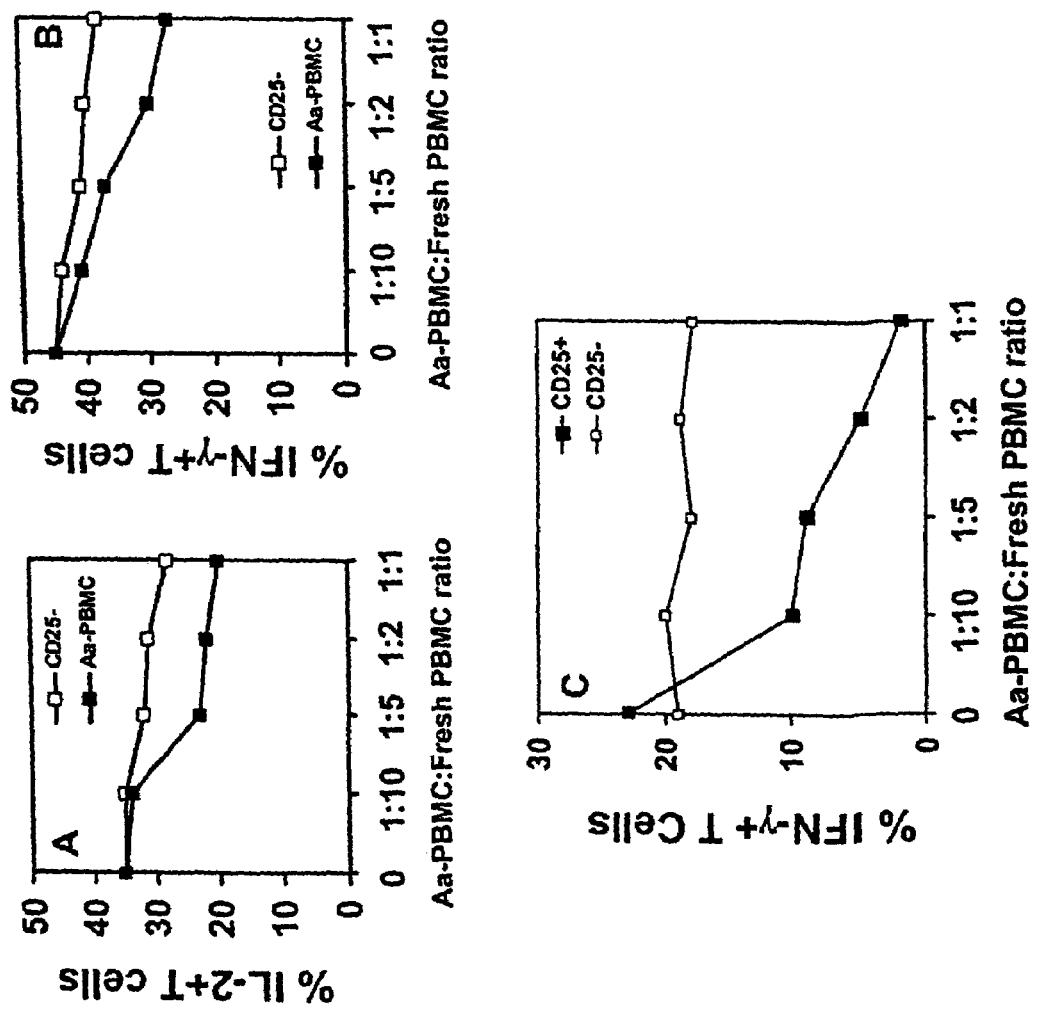
FIG. 3 shows dependence of hypo-responsiveness on the presence of $CD25^+$ cells.

Dependence of Hypo-Responsiveness on the Presence of CD4+CD25+ Cells. To begin to assess the role of the CD4+ CD25+ regulatory T cell subset in the induction of hypo-responsiveness, CD25+ cells were depleted prior to co-culture studies. Referring to FIG. 3, freshly isolated PBMC were incubated with *A. actinomycetemcomitans* antigenic preparation (25 μg/ml) for 48 hours. *A. actinomycetemcomitans*-stimulated cells were harvested, washed and the CD25+ and CD25− subsets were immunomagnetically separated. Freshly isolated PBMC were co-cultured at different ratios with either whole pre-stimulated PBMC (Aa-PBMC) or CD25-depleted pre-stimulated stimulated PBMC (CD25−) or pre-stimulated CD25+ or CD25− subsets for 4 hours in the presence of PMA and ionomycin. IL-2 and IFN-γ expression levels were measured with intracellular staining and analyzed by flow cytometry. Mean proportions of IL-2+ or IFN-γ+ T cells are shown. The data are representative of six independent experiments.

Results revealed a dose-dependent reduction of IL-2 (FIG. 3A) and IFN-γ (FIG. 3B) expression occurred in fresh PBMCs co-cultured in the presence of PBMC pre-stimulated with *A. actinomycetemcomitans* antigenic preparation. T cells stimulated with PMA and ionomycin were 35% IL-2+ and 45% IFN-γ+. Addition of PBMC pre-stimulated with *A. actinomycetemcomitans* antigenic preparation induced a diminution of IL-2 and IFN-γ expression. When 1:1 ratio of pre-stimulated to fresh PBMC were co-cultured and re-stimulated with PMA and ionomycin, 20% were IL-2+ and 30% were IFN-γ+. This may suggest that IL-2 and IFN-γ expression were reduced by 43% and 33%, respectively, when co-cultured with PBMC pre-stimulated with *A. actinomycetemcomitans* antigenic preparation. However, CD25-depleted PBMC pre-stimulated with *A. actinomycetemcomitans* had significantly reduced ability to suppress IL-2 and IFN-γ expression of fresh PBMC. When 1:1 ratio of CD25-depleted PBMC pre-stimulated with *A. actinomycetemcomitans* antigenic preparation to fresh PBMC were co-cultured and re-stimulated with PMA and ionomycin, 27% were IL-2+ and 37% were IFN-γ+. This indicated that IL-2 and IFN-γ expression were reduced by 22% and 17%, respectively, when co-cultured with CD25-depleted PBMC pre-stimulated with *A. actinomycetemcomitans* antigenic preparation.

To further investigate the role of CD4+CD25+ T cells, the CD25+ and CD25− subsets were separated from PBMC pre-stimulated with *A. actinomycetemcomitans* antigenic preparation and their suppressive capability was compared in co-culture studies. Accordingly, PBMC were stimulated with *A. actinomycetemcomitans* antigenic preparation for 48 hours followed by immunomagnetic separation of the CD4+CD25+ and CD4+CD25− subsets. Results in FIG. 3C indicate that the addition of CD4+CD25+ cells pre-stimulated with *A. actinomycetemcomitans* antigenic preparation induced a dose-dependent suppression of IFN-γ expression that was not observed when similarly-treated CD4+CD25− cells were added. When 1:1 ratio of pre-stimulated CD4+CD25+ cells to fresh PBMC were co-cultured and re-stimulated with PMA and ionomycin, the IFN-γ expression of PBMC was reduced from 22% to 2%. In contrast, in co-cultures containing the CD4+CD25− subset, IFN-γ expression remained at approximately 20%.

Figure 4:
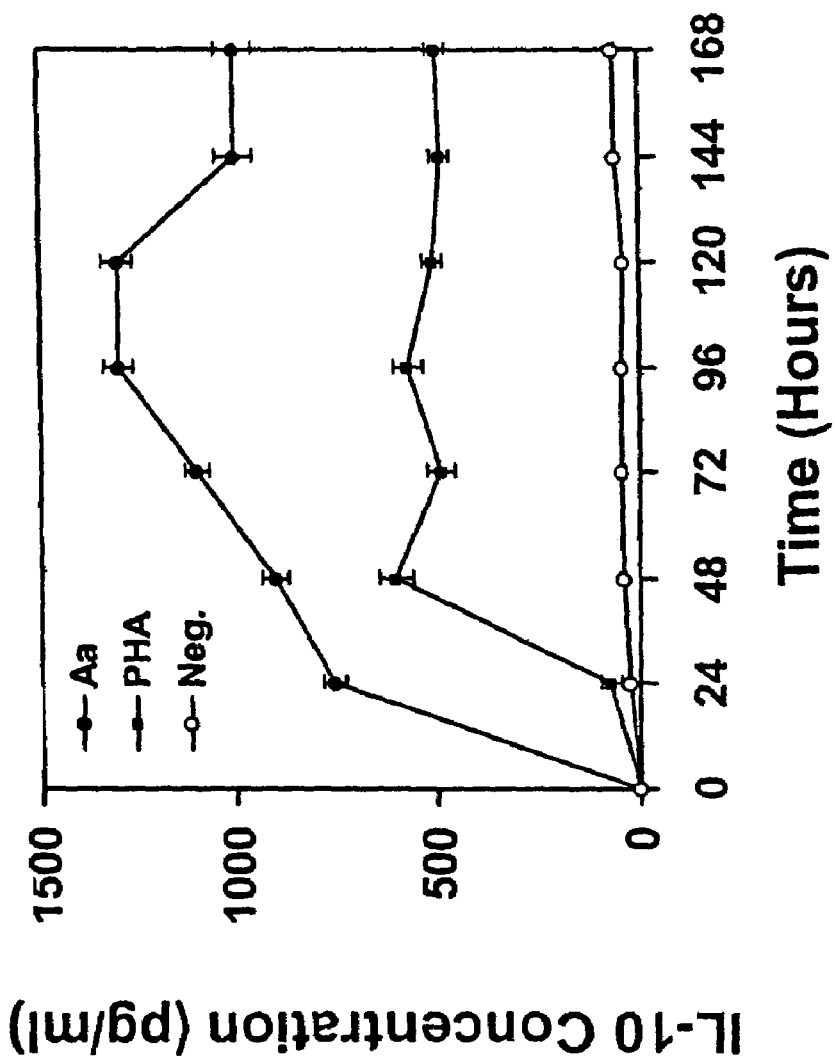
FIG. 4 shows IL-10 expression in response to *A. actinomycetemcomitans*.

Role of IL-10 in the Induction of Hypo-Responsiveness in *A. actinomycetemcomitans*-Treated PBMC. To investigate the cytokine mediators in the suppression of IL-2 and IFN-γ expression, the potential role of IL-10 was examined. Referring to FIG. 4, PBMC were incubated with *A. actinomycetemcomitans* antigenic preparation (50 μg/ml), PHA or SEE for 0-168 hours. Culture supernatants were collected and the presence of IL-10 was measured by a matched pair ELISA. Results reported (pg/ml) represent the average of two measurements. Data are representative of six independent experiments.

Results in FIG. 2 had previously demonstrated that nearly half of CD4+CD25+ T cells express IL-10. Next, the IL-10 level secreted in response to *A. actinomycetemcomitans* was quantitated. To that end, PBMC were stimulated with *A. actinomycetemcomitans* antigenic preparation for 48 hours. Culture supernatants were then harvested and IL-10 expression was measured by ELISA. The kinetics of IL-10 secretion demonstrated progressive increase in IL-10 level for the first 4 days of culture with *A. actinomycetemcomitans* antigenic preparation, reaching a peak level of 1300 pg/ml at 4 days (FIG. 4). The levels of IL-10 expression in response to *A. actinomycetemcomitans* antigenic preparation were 2.5 fold that observed after stimulation of PBMC with PHA or SEE.

Figure 5:
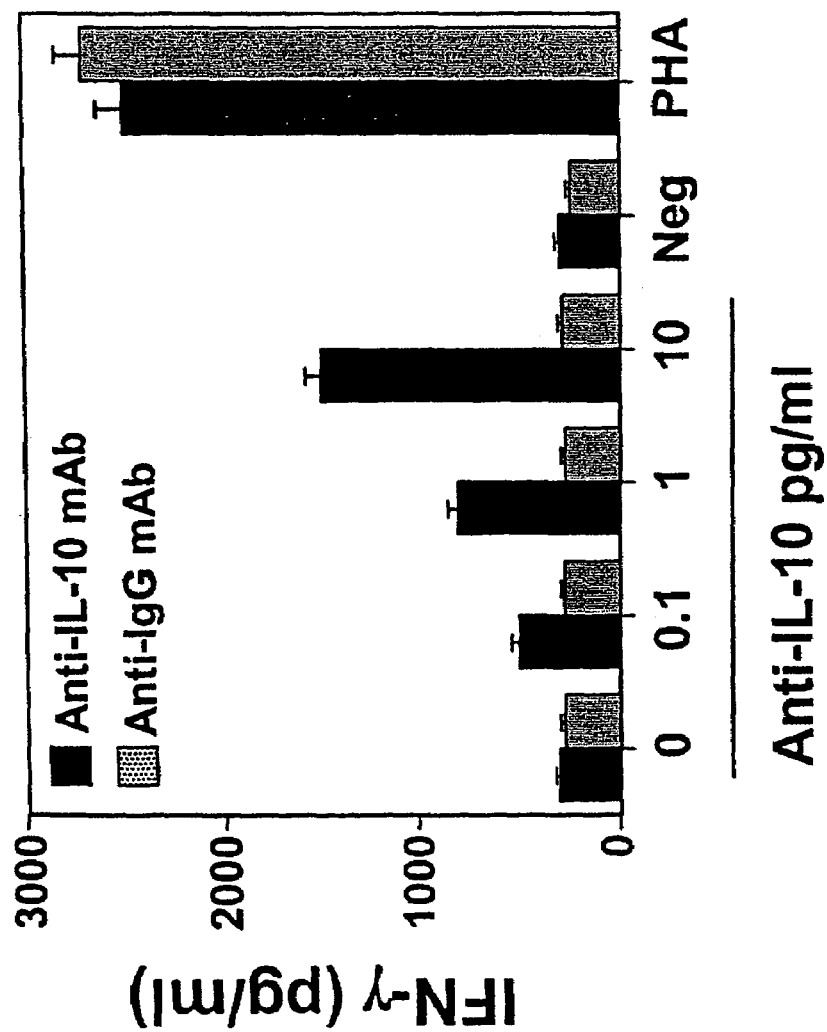
FIG. 5 shows the effect of IL-10 neutralization on the expression of IFN-γ in response to *A. actinomycetemcomitans*.

To determine whether the suppressive function of IL-10 on IFN-γ expression is reversible, IL-10 was neutralized by inclusion of anti-IL-10 monoclonal antibody in cell cultures. Accordingly, PBMC were stimulated with *A. actinomycetemcomitans* antigenic preparation in the presence of increasing concentrations of anti-IL-10 monoclonal antibody or isotype control monoclonal antibody for 48 hours. Referring to FIG. 5, PBMC were incubated with *A. actinomycetemcomitans* antigenic preparation (50 μg/ml) in the presence of 0.1 to 10 μg/ml mouse anti-human IL-10 or isotype control mouse IgG monoclonal antibodies. Culture supernatants were collected after 24 hours and the presence of IFN-γ was measured using a matched pair ELISA. For conversion of optical density values to IFN-γ concentration, the lower limit of sensitivity in this experiment was considered to be 25 pg/ml. The data are representative of three independent experiments, where the PBMC from a donor were cultured and analyzed in triplicate. Mean and S.E.M. of data are illustrated. Results presented in FIG. 5 demonstrated that there was a dose-dependent increase in IFN-γ secretion in the presence of anti-IL-10 monoclonal antibody.

Figure 6:
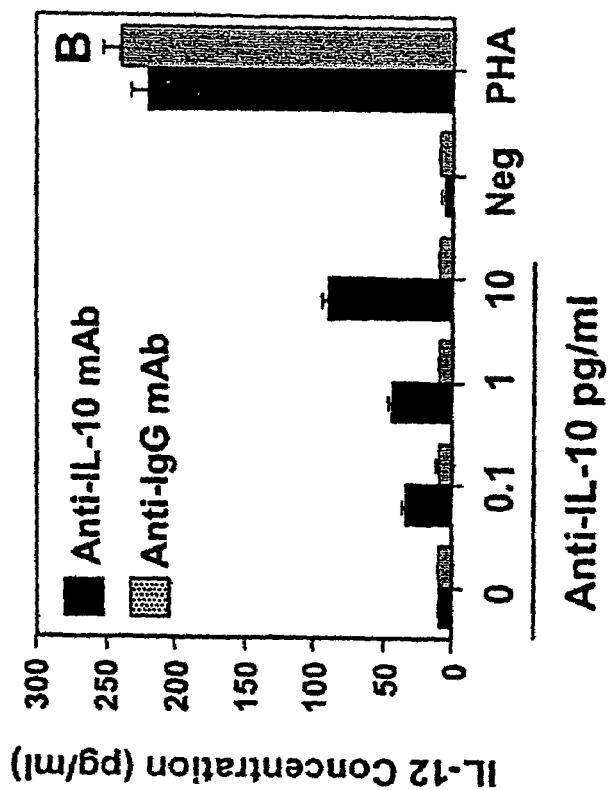
FIG. 6 shows IL-12 expression in response to *A. actinomycetemcomitans*.
Figure 6:
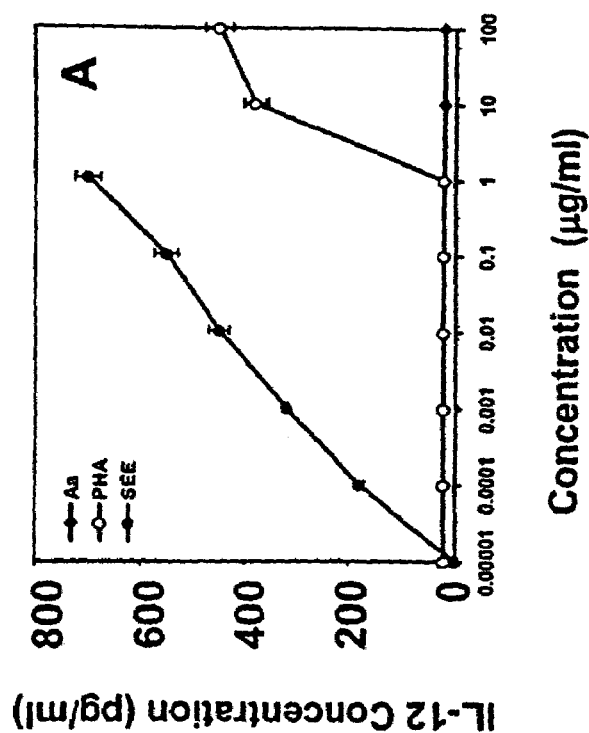

Next, the potential modulatory role of IL-10 on IL-12 expression was investigated. To that end, the presence of secreted IL-12 in culture supernatant of PBMC stimulated with *A. actinomycetemcomitans* antigenic preparation for various time points were assayed with ELISA. FIG. 6A shows dose response expression of IL-12 in response to *A. actinomycetemcomitans*. PBMC were incubated with varying concentration of *A. actinomycetemcomitans* antigenic preparation (0-100 μg/ml), PHA (0-50 μg/ml) or SEE (0-0.5 μg/ml) for 24 hours. Culture supernatants were collected and the presence of IL-12 was measured by a matched pair ELISA. FIG. 6B shows effect of IL-10 neutralization on the expression of IL-12 in response to *A. actinomycetemcomitans*. PBMC were incubated with *A. actinomycetemcomitans* antigenic preparation (50 μg/ml) in the presence of 0.1 to 10 μg/ml mouse anti-human IL-10 or isotype control mouse IgG monoclonal antibodies. Culture supernatants were collected after 24 hours and the presence of IL-12 was measured using a matched pair ELISA. For conversion of optical density values to IL-12 concentration, the lower limit of sensitivity in this experiment was considered to be 5.0 pg/ml. The data in panels A and B are representative of three independent experiments, where the PBMC from a donor were cultured and analyzed in triplicate. Mean and S.E.M. of data are illustrated. Results indicated non-detectable IL-12 in culture supernatant of PBMC stimulated with *A. actinomycetemcomitans* antigenic preparation (FIG. 6A). IL-12 expression was restored, in cultures stimulated with *A. actinomycetem-*

*comitans* antigenic preparation in the presence of anti-IL-10 monoclonal antibody (FIG. 6B).

Figure 7:
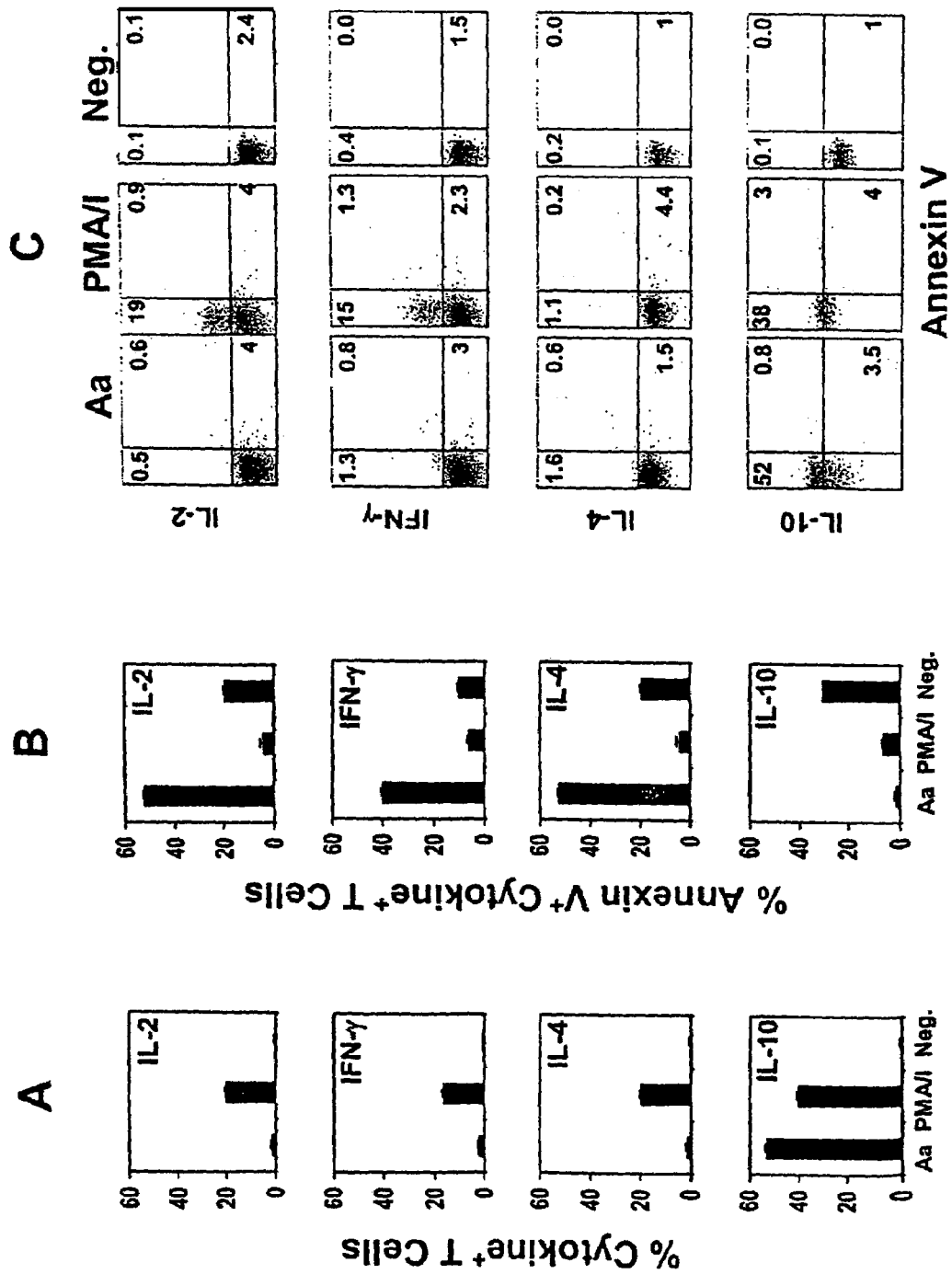
FIG. 7 shows expression of cytokines and induction of apoptosis among T cell subsets treated with *A. actinomycetemcomitans*.

The Relationship between Apoptosis and the Induction of Regulatory T Cells. In view of the potent ability of *A. actinomycetemcomitans* to induce apoptosis among T cells (Nalbant, A., et al., *Oral Microbiology and Immunology*, 15:290 (2000); Nalbant, A., et al., *Oral Microbiology & Immunology*, 17:277 (2002)) whether there was selective apoptosis among various functional subsets of T cells was determined. Referring to FIG. 7, PBMC were cultured with *A. actinomycetemcomitans* antigenic preparation for 4 hours, followed by intracellular cytokine staining in concert with Annexin V labeling assay and flow cytometry. PBMC were stimulated with *A. actinomycetemcomitans* antigenic preparation (Aa; 25 µg/ml), PMA (25 ng/ml) in conjunction with ionomycin (I; 1 µg/ml) or media alone (Neg.) for 4 hours. Cultured cells were first surface labeled with fluorochrome-conjugated Annexin V and anti-CD3 monoclonal antibody. Cells were then washed, permeabilized and intracellularly stained with fluorochrome-conjugated monoclonal antibodies specific for IL-2, IFN-γ, IL-4 and IL-10, followed by flow cytometric analysis. The data are representative of three independent experiments, where the PBMC from a donor were cultured and analyzed in triplicate. Mean and S.E.M. of the proportion of cytokine-positive T cells (A), as well as Annexin V-positive Cytokine-positive T cells (B) are shown. Representative flow cytometric profiles (C) show the raw data for the graphs in panels A and B. The expression of Annexin V (X-Axis) and cytokines (Y-Axis) is illustrated with the proportion of CD3$^+$ gated cells indicated in each window quadrant.

Results shown in FIG. 7A demonstrated that less than 1-2% of all T cells cultured with *A. actinomycetemcomitans* antigenic preparation expressed IL-2, IFN-γ or IL-4. This compared with approximately 23% being IL-10$^+$ ($p<0.05$). Conversely, approximately 40-50% of IL-2$^+$, IFN-γ$^+$ or IL-4$^+$ cells exhibited the apoptotic phenotype of extracellular Annexin binding, compared with nearly 3% of IL-10$^+$ ($p<0.05$) (FIG. 7B). Representative flow cytometric data (FIG. 7C) illustrate the raw data for the graphs, demonstrating the increased expression of IL-10 by *A. actinomycetemcomitans*-treated T cells and the reduced apoptosis among these IL-10$^+$ T cells.

Figure 8:
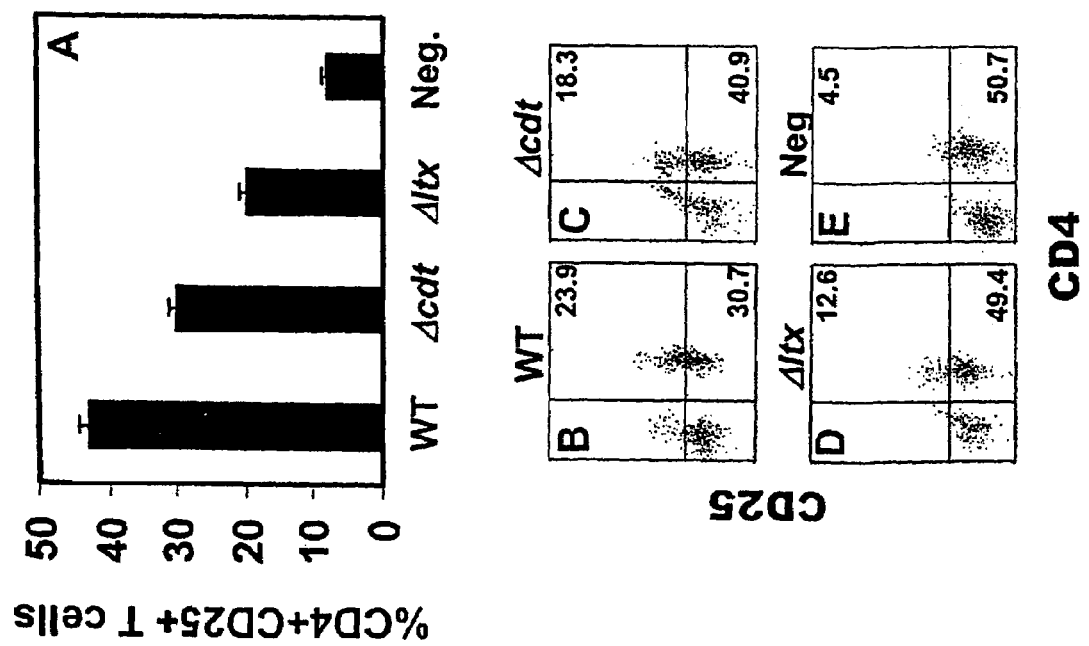
FIG. 8 shows the role cytolethal distending toxin (cdt) and leukotoxin (ltx) gene loci in the induction of regulatory T cells.

Role of cdt and ltx Gene Loci in the Induction of Regulatory T cells. To assess the relative contribution of *A. actinomycetemcomitans* CDT and leukotoxin to the induction of regulatory T cells, specific knockout mutant strains of cdt and ltx were examined. Freshly isolated PBMC were incubated for 48 hours with antigenic preparation of WT, Δltx or ΔcdtABC. The proportion of CD4$^+$CD25$^+$ T cells present among cultured cells was determined. Referring to FIG. 8, freshly isolated PBMC were incubated for 48 hours with antigenic preparation of *A. actinomycetemcomitans* wild type (WT), ΔcdtABC, ΔltxA or negative control (Neg.), where stimuli were omitted. Cultured cells were labeled with anti-CD25, anti-CD3 and anti-CD4 monoclonal antibodies, followed by flow cytometric analysis. The data are representative of five independent experiments, where the PBMC from a donor were cultured and analyzed in triplicate. Mean and S.E.M. of the proportion of CD25-positive CD4-positive T cells are shown (A). Representative flow cytometric profile of CD25-positive CD4 positive T cells exposed to wild type (B), specific cdtABC knockout mutant (C), specific ltxA knockout mutant (D) of *A. actinomycetemcomitans* antigenic preparation and media alone (E) are shown.

Results in FIG. 8A demonstrated a significant reduction in the proportion of CD4$^+$CD25$^+$ T cells among cells cultured in the presence of $^{ltx}$ ($p<0.05$) and ΔcdtABC ($p<0.05$) antigenic preparations, compared with those cultured with WT antigenic preparation. Representative flow cytometric profile of CD4$^+$CD25$^+$ T cells exposed to *A. actinomycetemcomitans* antigenic preparations of WT (FIG. 8B), ΔcdtABC (FIG. 8C), ΔltxA (FIG. 8D) or media alone (E) are shown.

Figure 9:
FIG. 9 shows the role cdt and ltx gene loci in the induction of IL-10 and IFN-γ by regulatory T cells.

The expression of IL-10 and IFN-γ among cells cultured with antigenic preparations of WT parent and isogenic Δltx or ΔcdtABC strains was determined by intracellular cytokine staining. Referring to FIG. 9, freshly isolated PBMC were incubated for 48 hours with antigenic preparation of *A. actinomycetemcomitans* wild type (WT), ΔcdtABC, ΔltxA or negative control (Neg.), where stimuli were omitted. Cultured cells were labeled with anti-CD25, anti-CD3 and anti-IL-10 or anti-IFN-gamma monoclonal antibody, followed by flow cytometric analysis. The data are representative of three independent experiments, where the PBMC from a donor were cultured and analyzed in triplicate. Mean and S.E.M. of the proportion of IL-10 positive T cells among CD25-positive versus CD25-negative T cells (A) as well as IFN-gamma positive T cells among CD25-positive versus CD25-negative T cells (B) are shown.

Results shown in FIG. 9 demonstrated that a significantly higher proportion of T cells cultured with WT antigenic preparation were IL-10$^+$, compared with those cells cultured in the presence of antigenic preparation of Δltx ($p<0.05$) or ΔcdtABC ($p<0.05$) strains (FIG. 9A). Conversely, a significantly lower proportion of T cells cultured with WT antigenic preparation were IFN-γ$^+$, compared with those cells cultured in the presence of antigenic preparation of isogenic Δltx ($p<0.05$) or ΔcdtABC ($p<0.05$) strains (FIG. 9B).

Discussion

The results of the present study demonstrated high levels of IL-10 expression, while IL-12 was undetectable. Lack of IL-2 and IFN-γ, coupled with low IL-4 and high IL-10 among T cells stimulated with *A. actinomycetemcomitans* preparations suggests that these cells are functionally distinct from Th2 T cells. The present data also suggests that the IL-10 producing T cells predominantly express the CD4$^+$CD25$^+$ antigenic phenotype, which is characteristic of regulatory T cells. The discovery that the suppressive effects of *A. actinomycetemcomitans* are reversed by neutralizing IL-10, suggests the involvement of type 1 regulatory T cells (Tr1). Co-culture studies demonstrated that PBMC, in particular the CD4$^+$CD25$^+$ subset, which had previously been exposed to preparations of *A. actinomycetemcomitans*, suppress the expression of IFNγ and IL-2.

Based on experimental data, dichotomous functions may be attributed to regulatory T cells. On the one hand, impairment of immune response, such as reported here, as well as by others (Shevach, E. M., 2:389 (2002)), may contribute to the persistence of pathogens in vivo. On the other hand, regulatory T cells may also function to contain an exuberant immune response, as suggested by other data (Kullberg, M., et al., *The Journal of Experimental Medicine*, 196:505 (2002)).

The diminution in the proportion of CD4$^+$CD25$^-$ and IL-10$^+$ T cells and the concomitant rise in the proportion of IFN-γ$^+$ T cells among T cells stimulated with isogenic Δltx or ΔcdtABC strains was of interest. One explanation is that leukotoxin and CDT may be responsible for the induction of CD4$^+$ CD25$^-$ T cells. Alternatively, in view of the relative resistance of CD4$^+$CD25$^-$ T cells to apoptosis (Banz, A., et al., *Journal of Immunology*, 169:750 (2002)), it is possible that apoptotic killing of T cells by leukotoxin and CDT may lead to the selective survival of CD4$^+$CD25$^+$ T cells. Another model is that the suppression of IFN-γ expression is partly due to apoptotic killing of responder cells and that deletion of cytotoxins diminishes the ability of *A. actinomycetemcomitans* to kill these responders.

The inventor's results reveal the central role of IL-10 in the suppressive effects of *A. actinomycetemcomitans* preparation on Th1 cytokine expression. Firstly, high levels of IL-10 were expressed by T cells and released in culture fluid when PBMC were cultured in the presence of *A. actinomycetemcomitans* preparations. Secondly, neutralization of IL-10 by monoclonal antibodies leads to an increase in the expression of IFN-γ and IL-12. Thirdly, deletion of genes for cytotoxins such as cdt and ltx resulted in decreased induction of IL-10 expression relative to the levels induced by WT. Under these conditions, a concomitant increased induction of IFN-γ cytokine expression was observed.

The foregoing description is considered as illustrative only of the principles of the invention. Further, since numerous modifications and changes will readily occur to those skilled in the art, it is not desired to limit the invention to the exact construction and process shown as described above. Accordingly, all suitable modifications and equivalents may be resorted to falling within the scope of the invention as defined by the claims that follow. The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

The embodiments of the invention in which an exclusive property or privilege is claimed are defined as follows:

1. A method of generating regulatory cells comprising:
   incubating one or more proteins comprising a cytolethal distending toxin (cdt), a leukotoxin (ltx) and/or a heat shock protein with blood cells for a time sufficient to induce differentiation, selective enrichment, and/or promoting proliferation of regulatory T cells, wherein said proteins are secreted from at least one pathogenic organism, wherein said pathogenic organism that secretes leukotoxin is *Actinobacillus actinomycetemcomitans, Mannheimia (Pasteurella) haemolytica*, or *Fusobacterium necrophorum*.

2. A method of generating regulatory cells comprising:
   incubating one or more proteins comprising a cytolethal distending toxin (cdt), a leukotoxin (ltx) and/or a heat shock protein with blood cells for a time sufficient to induce differentiation, selective enrichment, and/or promoting proliferation of regulatory T cells, wherein said proteins are secreted from at least one pathogenic organism, wherein said pathogenic organism that secretes a cytolethal distending toxin is *Actinobacillus actinomycetemcomitans, Escherichia coli Shigella dysentarie, Haemophilus ducreyi, Campylobacter upsaliensis, Campylobacter jejuni Helicobacter hepaticus*, and *Salmonella. enterica* serovar Typhi genome.

3. The method of claim 1, wherein said proteins are in a crude extract.

4. The method of claim 1, wherein said proteins are in a purified form.

5. A method of generating regulatory cells comprising:
   incubating one or more proteins comprising a cytolethal distending toxin (cdt), a leukotoxin (ltx) and/or a heat shock protein with blood cells for a time sufficient to induce differentiation, selective enrichment, and/or promoting proliferation of regulatory T cells, wherein said proteins are expressed from at least one expression plasmid.

6. A method of generating regulatory cells comprising:
   incubating one or more proteins comprising a cytolethal distending toxin (cdt), a leukotoxin (ltx) and/or a heat shock protein with blood cells for a time sufficient to induce differentiation, selective enrichment, and/or promoting proliferation of regulatory T cells, wherein said heat shock gene is GroEL.

7. A method of generating regulatory cells comprising:
   incubating one or more proteins comprising a cytolethal distending toxin (cdt), a leukotoxin (ltx) and/or a heat shock protein with blood cells for a time sufficient to induce differentiation, selective enrichment, and/or promoting proliferation of regulatory T cells, wherein said blood cells are concentrated peripheral blood mononuclear cells.

8. A method of generating regulatory cells comprising:
   incubating one or more proteins comprising a cytolethal distending toxin (cdt), a leukotoxin (ltx) and/or a heat shock protein with blood cells for a time sufficient to induce differentiation, selective enrichment, and/or promoting proliferation of regulatory T cells, wherein said regulatory T cells are Tr1.

9. A method of inducing differentiation and promoting proliferation of regulatory T cells comprising:
   incubating peripheral blood mononuclear cells in the presence of at least three proteins, cytolethal distending toxin (cdt), leukotoxin (ltx) and a heat shock protein; and selecting for Tr1 cells.

10. The method of claim 9, wherein said proteins are secreted from a pathogenic organism.

11. The method of claim 10, wherein said pathogenic organism is *Actinobacillus actinomycetemcomitans*.

12. The method of claim 9, wherein said proteins are introduced into said peripheral blood mononuclear cells in a purified form.

13. The method of claim 9, wherein said proteins are introduced into said peripheral blood mononuclear cells as a crude extract.

14. The method of claim 9, wherein said proteins are introduced into said peripheral blood mononuclear cells by way of an expression vector.

15. A composition comprising an expression vector comprising a coding sequence for a cytolethal distending toxin (cdt), a leukotoxin (ltx) and a heat shock protein.

16. The expression vector of claim 15, further comprising a liposome.

17. The expression vector of claim 16, for use as an immunosuppressant agent.

18. The method of claim 2, wherein said proteins are in a crude extract.

19. The method of claim 2, wherein said proteins are in a purified form.

* * * * *